(12) United States Patent
Steinberg et al.

(10) Patent No.: US 9,937,278 B2
(45) Date of Patent: Apr. 10, 2018

(54) BIOCOMPATIBLE AND BIODEGRADABLE GRADIENT LAYER SYSTEM FOR REGENERATIVE MEDICINE AND FOR TISSUE SUPPORT

(75) Inventors: Thorsten Steinberg, Mannheim (DE); Pascal Tomakidi, Teningen (DE); Simon Schulz, Freiburg (DE); Marco Angarano, Ettlingen (DE); Rolf Muelhaupt, Freiburg (DE); Martin Fabritius, Freiburg (DE)

(73) Assignee: AMOR (SUZHOU) MEDICAL SCI-TECH CO., LTD., Suzhou New and Hi-Tech Zone (CN)

( * ) Notice: Subject to any disclaimer, the term of this patent is extended or adjusted under 35 U.S.C. 154(b) by 0 days.

(21) Appl. No.: 14/110,031

(22) PCT Filed: Apr. 4, 2012

(86) PCT No.: PCT/EP2012/056155
§ 371 (c)(1),
(2), (4) Date: Dec. 17, 2013

(87) PCT Pub. No.: WO2012/136701
PCT Pub. Date: Oct. 11, 2012

(65) Prior Publication Data
US 2014/0112973 A1 Apr. 24, 2014

(30) Foreign Application Priority Data

Apr. 5, 2011 (EP) ..................... 11002836

(51) Int. Cl.
*A61L 26/00* (2006.01)
*A61L 27/34* (2006.01)
*A61L 27/38* (2006.01)
*A61L 27/50* (2006.01)
*A61L 27/58* (2006.01)
*A61L 31/12* (2006.01)
*A61L 31/16* (2006.01)

(52) U.S. Cl.
CPC .......... *A61L 26/0095* (2013.01); *A61L 27/34* (2013.01); *A61L 27/3804* (2013.01); *A61L 27/50* (2013.01); *A61L 27/58* (2013.01); *A61L 31/125* (2013.01); *A61L 31/16* (2013.01); *A61L 2420/08* (2013.01)

(58) Field of Classification Search
None
See application file for complete search history.

(56) References Cited

U.S. PATENT DOCUMENTS

| 2002/0090725 A1 | 7/2002 | Simpson et al. |
| 2004/0116032 A1 | 6/2004 | Bowlin et al. |
| 2009/0074832 A1 * | 3/2009 | Zussman et al. ............. 424/423 |

FOREIGN PATENT DOCUMENTS

| EP | 0 674 891 A2 | 10/1995 | |
| WO | 2006/106506 A2 | 10/2006 | |
| WO | WO2010041944 * | 4/2010 | ............... D04H 1/42 |
| WO | 2010/084481 A1 | 7/2010 | |

OTHER PUBLICATIONS

Quideau et al. (Plant polyphenols chemical properties, biological activities, and synthesis, Angew. Chem. Int. Ed., 2011, vol. 50, pp. 586-621, available online by Jan. 7, 2011).*
McClure et al. (A three-layered electrospun matrix to mimic native arterial architecture using polycaprolactone, elastin and collagen: A preliminary study, Acta Biomaterialia, 2010, vol. 6, pp. 2422-2433).*
Arnoult (A novel benigh solution for collagen processing, Thesis, Case Western University, May 2010).*
Hu et al. (cell immobilization in gelatin-hydroxyphenylpropionic acid hydrogel fibers, Biomaterials, 2009, vol. 30, pp. 3523-3531).*
Yeo et al. (Three-Dimensional Hierarchical Composite Scaffolds Consisting of Polycaprolactone, β-Tricalcium Phosphate, and Collagen Nanofibers: Fabrication, Physical Properties, and In Vitro Cell Activity for Bone Tissue Regeneration, Macromolecules, 2011, vol. 12, pp. 502-510, published on Dec. 28, 2010).*
International Search Report dated Jul. 30, 2012, in corresponding International Application No. PCT/EP2012/056155.

* cited by examiner

*Primary Examiner* — Bethany P Barham
*Assistant Examiner* — Ping Cao
(74) *Attorney, Agent, or Firm* — Squire Patton Boggs (US) LLP

(57) ABSTRACT

The present invention is directed to a biocompatible and preferably biodegradable gradient layer system comprising at least one set of layers comprising a biocompatible and preferably biodegradable cross-linked polymer and at least one biocompatible and preferably biodegradable support layer, wherein a gradient is preferably formed with respect to the mechanical and/or physical properties of one or more layers of the at least one set of layers comprising a biocompatible and biodegradable cross-linked polymer and/or the at least one biocompatible and preferably biodegradable support layer. The at least one support layer preferably comprises a biocompatible and preferably biodegradable meltable polymer and/or a biocompatible and incorporable material. This biocompatible and preferably biodegradable gradient layer system may be used as a biomaterial for regenerative medicine, particularly as a wound dressing or for tissue support. The present invention also provides means utilizing said inventive gradient layer system and methods for producing same.

9 Claims, 3 Drawing Sheets

Figure 1:
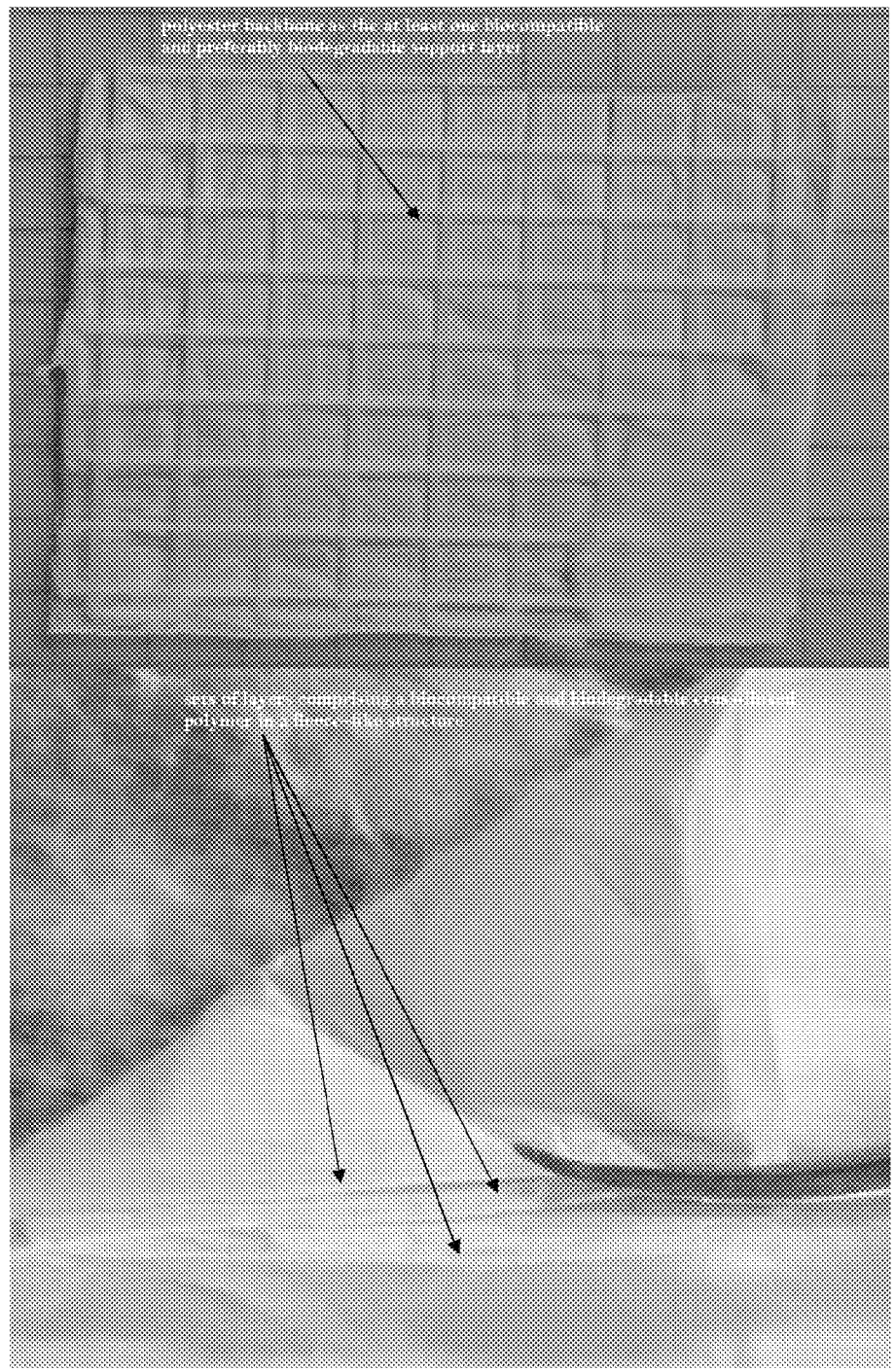

BIOCOMPATIBLE AND BIODEGRADABLE GRADIENT LAYER SYSTEM FOR REGENERATIVE MEDICINE AND FOR TISSUE SUPPORT

The present invention is directed to a biocompatible and preferably biodegradable gradient layer system comprising at least one set of layers comprising a biocompatible and preferably biodegradable cross-linked polymer and at least one biocompatible and preferably biodegradable support layer, wherein a gradient is preferably formed with respect to the mechanical and/or physical properties of one or more layers of the at least one set of layers comprising a biocompatible and biodegradable cross-linked polymer and/or the at least one biocompatible and preferably biodegradable support layer. The at least one support layer preferably comprises a biocompatible and preferably biodegradable meltable polymer and/or a biocompatible and incorporable material. This biocompatible and preferably biodegradable gradient layer system may be used as a biomaterial for regenerative medicine, particularly as a wound dressing or for tissue support. The present invention also provides means utilizing said inventive gradient layer system and methods for producing same.

In regenerative medicine epithelial burn traumata represent cases of increasing incidence. Treatment of such large wounds typically occurs by removing the damaged tissue completely. Subsequently, healthy skin is transplanted from an unaffected region of the patient to the wound to be treated. Necessarily, transplantation of skin grafts requires invasive surgery and involves large areas of the skin. These treatments are therefore not only painful but also bear the risk of infection, the formation of scars and may be accompanied by impaired wound healing due to the excessive size of the wounds.

Novel approaches have shown that such wounds also may be treated by new biomaterials developed for regenerative medicine, in particular wound dressing materials. In this context, biomaterials for regenerative medicine should have abilities including the removal of exudates and protection of the wound but also sufficient mechanical properties as they have to resist shear forces typically occurring locally in tissues and transplants. There are several further characteristics of the ideal wound dressing material which could satisfy these requirements, such as a high porosity for gas permeation and a good barrier for protection of the wound from infection and dehydration. Based on these requirements, candidate biomaterials developed for regenerative medicine, in particular wound dressing materials, must be assessed to verify that they are both good barriers and have good oxygen permeability. Additionally, such materials shall ideally support the growth of new tissue on the wound and thus preferably resemble the scaffold structure of the tissue to be replaced or at least a scaffold structure which allows ingrowth of cells and/or neovascularization of the scaffold structure.

Biomaterials for regenerative medicine, which may be suitable for such purposes, are preferably composed of biocompatible materials. Many examples of biocompatible materials are shown in the art, only some of which may be used effectively due to mechanical and physical limitations of the respective materials.

Generally, materials used in the art may be distinguished into naturally occurring polymers and synthetic polymers. Naturally occurring polymers typically show good biocompatibility and biodegradability. Synthetic polymers, in part, may also show a good biocompatibility and in part biodegradability. However, preparation of such synthetic polymers often requires application of cytotoxic substances such as catalysts, cytotoxic solvents, and/or such polymers may comprise monomers or organic solvents. These impurities cannot be removed entirely and thus may remain as a cytotoxic component in the final polymer. Such impurities inter alia may lead to inflammation reactions of the surrounding tissue, to unwanted immune reactions of the patient to be treated at the transplantation site and even to allergies or graft rejection reactions of the transplant.

One prominent naturally occurring polymer, which provides very good biocompatibility and even more preferred a good biodegradability, is gelatin. Gelatin is a protein that is widely used in the pharmaceutical and food industries, and it is produced on a large scale at relatively low prices. It also shows a limited barrier to water vapor, a feature, which is particularly advantageous for preparation of efficient wound dressing materials. Due to its functional properties it has been utilized furthermore in the production of edible and/or biodegradable films. However like the majority of protein-based films, it has limited mechanical properties and shows a poor stability and resistance to shearing forces, which renders application difficult as biomaterials for regenerative medicine.

Many attempts in the art thus try to provide improved biomaterials on the basis of gelatin, to obtain a good or improved mechanical stability by admixing gelatin in a combined polymer solution with a synthetic and mechanically more stable polymer. Such synthetic and mechanically more stable polymers are, e.g., polycaprolactone (PCL), poly(lactic acid) (PLA), poly(lactic-co-glycolic acid) (PLGA), polyurethane (PU), etc. Such mixed polymers, however, significantly reduce the superior qualities of gelatin and of other naturally occurring polymers as they reduce the limited barrier to water vapor, diminish or even extinguish the superior biocompatibility properties of gelatin and even may lead to inflammation reactions of the surrounding tissue, to unwanted immune reactions of the patient to be treated at the transplantation site and even to allergies or graft rejection reactions of the transplant due to use of cytotoxic solvents already discussed for synthetic polymers alone.

One such approach is discussed e.g. in US patent application US 2002/0090725 A1, which discloses electroprocessed collagen but also electroprocessed mixed polymer compositions comprising collagen in combination with synthetic polymers such as poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), synthetic polycations (such as poly(ethylene imine)), synthetic polyanions (such as poly(styrene sulfonate) and poly(methacrylic acid)), poly(methacrylic acid), polylactic acid (PLA), polyglycolic acids (PGA), poly(lactide-coglycolides) (PLGA), nylons, polyamides, polyanhydrides, poly(ethylene-co-vinyl alcohol) (EVOH), polycaprolactone, poly(vinyl acetate) (PVA), poly(ethylene oxide) (PEO) and polyorthoesters or other similar synthetic polymers that may be developed that are biologically compatible. Unfortunately, only some of these synthetic polymers are biodegradable and thus need to be removed subsequent to application, if they can not or are not to be incorporated into the body permanently. Such non-biodegradable polymers are therefore suitable for temporary applications. Additionally, even though the mixed polymers of US 2002/0090725 A1 may show enhanced mechanical properties, they do not remove the disadvantage of possible unwanted side reactions as discussed above. Furthermore, such materials and polymer matrices made thereof only provide limited capabilities with respect to ingrowth of cells, water and vapor permeability, etc.

A further approach in US 2003/0232746 is directed to a stabilized cross-linked hydrogel matrix comprising a first high molecular weight component and a second high molecular weight component. Both high molecular weight components are covalently cross-linked, wherein the first high molecular weight component and the second high molecular weight component are each selected from the group consisting of polyglycans and polypeptides, preferably any tissue-derived or synthetically produced polypeptide, such as collagens or collagen-derived gelatins, more preferably dextran and gelatin. The composition additionally contains at least one stabilizing or enhancing agent. Even though providing for a multitude of different functions and improved mechanical properties, the stabilized cross-linked hydrogel matrices of US 2003/0232746, require crosslinkers in the preparation of the matrices, which may not be removed sufficiently after cross-linking and thus retain in the final polymer matrix. As mentioned above, such remnants may lead to allergic reactions and inflammation reactions of the surrounding tissue as already discussed above but may also lead to cytotoxic effects due to non-reacted cross-linker compounds.

A further document, Lelkes et al. (US 2006/0263417), discloses electrospun blends of natural and synthetic polymeric fibers as tissue engineering scaffolds. As discussed initially in Lelkes et al., co-spinning was intended as a first approach with each material in a different syringe and applying the materials at the same time on a support via electrospinning to provide mechanically improved but still porous matrices. This approach, however, was discarded by the authors. Instead, the authors recognized that a material may be advantageous, that exhibits a less dense fibrous network. As a solution for this problem, Lelkes et al. (US 2006/0263417) suggest a fiber comprising an electroprocessed blend of at least one synthetic polymer and at least two natural polymers without crosslinking. Preferably, one of the at least two natural polymers is elastin or a pro-form of elastin or an elastin-like material. Such matrices Lelkes et al. (US 2006/0263417) were intended to exhibit a more porous scaffold than prior art matrices and observed to remain stable in cell culture medium. However, a blend of different naturally occurring and synthetic materials as favored by Lelkes et al. (US 2006/0263417), significantly alters and corroborates the superior qualities of these polymers due to blending same in one polymer mix as already discussed above.

Another approach to improve the mechanical properties of gelatin is reported by Carvalho et al. (see Carvalho et al., Brazilian Journal of Chemical Engineering, Vol. 23, No. 01, pp. 45-53, January-March, 2006), even though in another context. As discussed therein, gelatin films were prepared for edible and/or biodegradable films, wherein the gelatin was further crosslinked. As a result, the increase in degree of cross-linking causes a reduction in water vapor permeability through the reduction in diffusivity and an improvement of mechanical characteristics. However, a high cross-linking ratio is less preferable as it results in particularly small pores and significantly reduces a possible ingrowth of cells.

A similar approach as discussed before is described in Lee et al. (US 2008/0233162 A1). Lee et al. disclose a fibrous porous 3-dimensional scaffold for tissue regeneration comprising a polymer and/or a low molecular fiber. This polymer and/or the low molecular fiber is a biodegradable polymer composed of one or more synthetic bio-degradable aliphatic polyesters or one or more natural polymers. The polymers are formed in a 3-dimensional network structure by electrospinning and may be used alone or together in a mix of polymers. Lee et al. (US 2008/0233162 A1), however, do not provide further alternatives, which may overcome the underlying problems.

Kim et al. (see Kim et al., Biomed. Mater. 4, (2009) 044106 (11p)) disclose a blended nanofiber scaffold using synthetic and natural polymers, polyurethane (PU) and gelatin respectively, using the electrospinning method to prepare a material for wound dressing. They determined the properties of this gelatin/PU blended nanofiber scaffold and found that the mean diameter of these nanofibers was uniformly electrospun and ranged from 0.4 to 2.1 µm. According to the results, when the amount of gelatin in the blended solution decreased, the contact angle increased and water uptake of the scaffold decreased concurrently. In the mechanical tests, the blended nanofibrous scaffolds were elastic, and elasticity increased as the total amount of PU increased. Moreover, as the total amount of gelatin increased, the cell proliferation increased with the same amount of culture time. However, although this gelatin/PU blended nanofiber scaffold has potential application for use as a wound dressing, the superior properties of the natural polymers of the scaffold are still impaired by blending same with a further polymer.

US 2010/0129450 is directed to compositions and methods for preparing electrospun matrices comprising at least one natural biological material component and at least one synthetic polymer material. The natural component makes the matrices highly biocompatible while the molecular weight polymer component can impart additional mechanical strength to the scaffold and/or improve ease of manufacture by increasing viscosity and spinning characteristics of the solution during electrospinning. Similar as discussed for other methods and scaffolds in the art, US 2010/0129450 utilizes a blend of different polymers in the preparation of the electrospun matrix. As already stated, such blends may impair the superior properties of natural polymers of the scaffold by blending same with a further polymer and thus may only provide limited properties with regard to e.g. gas permeation and dehydration or may not sufficiently allow ingrowth of cells and formation of a novel tissue structure.

Summarizing the above, biomaterials provided by the prior art methods still suffer from several disadvantages, such as poor cell ingrowth, insufficient mechanical stability, cytotoxicity, etc. Accordingly, it is the object of the present invention to provide new biomaterials for regenerative medicine, preferably for wound dressings and support of tissue, which allow to effectively cultivate cells in its scaffold structure, shows good mechanical properties, a high porosity for gas permeation and a good barrier for protection of the wound from infection and dehydration, but does not corroborate the superior quality of the applied natural or synthetic polymers. Furthermore, such biomaterials shall support effectively ingrowth of cells and formation of a new tissue structure, e.g. an extracellular membrane or a functional organ tissue.

This object underlying the present invention is solved by the claims attached to the present disclosure.

Preferably, according to a first embodiment the object underlying the present invention is solved by a biocompatible and preferably biodegradable gradient layer system comprising at least one set of layers comprising a biocompatible and preferably biodegradable cross-linked polymer and at least one biocompatible and preferably biodegradable support layer, wherein a gradient is preferably formed with respect to the mechanical and/or physical properties of one or more layers of the at least one set of layers comprising a biocompatible and biodegradable cross-linked polymer and/or the at least one biocompatible and preferably biodegradable support layer. Preferably, a gradient is formed by altering the mechanical and/or physical properties either within the at least one layer or set of layers or between several layers or sets of layers of the inventive gradient layer system. Preferably, mechanical and/or physical properties comprise e.g. mechanical strength, pore size, fiber strength, fiber length, etc. Fiber strength particularly means the width or diameter of a fiber, which in turn typically determines the mechanical strength of the fiber. In the context of the present invention, the term "fiber strength" is thus preferably referred to the width or diameter of a fiber as defined herein. The biocompatible and preferably biodegradable gradient layer system is preferably water insoluble.

The present invention effectively allows, due to the inventive biocompatible and preferably biodegradable gradient layer system, an adaption of the present system to a multiplicity of different situations occurring in the treatment of wounds. The inventive gradient layer system provides for a novel and flexible biomaterial with a good biocompatibility with broad application in the treatment of burns, the treatment of lesions or wounds due to surgical treatments, cancer, or other diseases but also the treatment of chronic wounds and in reconstructive plastic surgery. The inventive gradient layer system furthermore can be easily adapted to different biomechanical needs of e.g. a wound or lesion to be treated. The inventive gradient layer system can furthermore be supplemented with a multitude of different compounds, such as growth factors, interleukins, etc. It additionally shows a timely retarded degradation in vivo due to the adjustable mechanical strength of the inventive gradient layer system in its different layers or sets of layers. This allows a tissue, supplemented with such an inventive gradient layer system, to effectively replace the inventive gradient layer system by growing into said artificial tissue or scaffold during short or long term treatments of wounds. It also allows a slow degradation of the inventive gradient layer system, preferably for use in soft tissue structures, and/or an incorporation of the inventive gradient layer system, preferably for use in hard tissue structures. The inventive gradient layer system as such also allows to effectively and comprehensively cultivate the sets of layers or layers with e.g. autologous cells due to the consistent structure of the inventive gradient layer system. This effectively allows the preparation of artificial tissue constructs and even of artificial organs including establishing a functional vascular system in said artificial tissue construct or organ. Furthermore, antimicrobial polymers (AMPs) may be integrated into the polymers or the electro-spun polymeric fibers The inventive biocompatible and preferably biodegradable gradient layer system may be utilized as a biomaterial for regenerative medicine, particularly as a wound dressing or for tissue support, particularly for soft and/or hard tissue support. It is preferably biocompatible, biodegradable, water insoluble and effectively supports ingrowth of cells into its scaffold structure and formation of a new tissue structure, e.g. an extracellular matrix and/or membrane, a functional organ tissue or any further tissue. It furthermore shows good mechanical properties and does not corroborate the superior quality of the applied natural or synthetic polymers.

The first embodiment of the present invention defines a biocompatible and preferably biodegradable gradient layer system comprising at least one set of layers comprising a biocompatible and preferably biodegradable cross-linked polymer.

In this context, the term "set of layers" may be preferably interpreted as a 3-dimensional arrangement of at least one "single layer", e.g. of polymeric fibers or any other compound. Accordingly, such a "set of layers" may be composed of one or more "single layers", i.e. the set of layers may comprise e.g. 1, 2, 3, 4, 5, 6, 7, 8, 9, 10, 1-15, 10-25, 15-30, 10-50 or 10-100 or even more "single layers". Thus, a "set of layers" in this context may be understood as sort of a non-woven fleece, a mat, or a fleece like or mat like structure comprising one or more single layers, e.g. 1, 2, 3, 4, 5, 6, 7, 8, 9, 10, 1-15, 10-25, 15-30, 10-50 or 10-100 or even more, due to the production of the such a "set of layers".

Furthermore, the term "gradient layer system" is preferably to be understood as a layer system comprising layers or sets of layers as defined herein, wherein these layers or sets of layers form a gradient with respect to the mechanical and/or physical properties, either within the at least one layer or set of layers or between several layers or sets of layers of the inventive gradient layer system. Preferably, the gradient is formed with respect to the mechanical and/or physical properties of the at least one set of layers comprising a biocompatible and biodegradable cross-linked polymer and the at least one biocompatible and preferably biodegradable support layer, preferably by altering, increasing or decreasing mechanical and/or physical properties, e.g. mechanical strength, pore size, fiber strength, fiber length, etc. of one or more of such layers or sets of layers. Accordingly, such a gradient may alter within one set of layers comprising a biocompatible and biodegradable cross-linked polymer, from one set of layers comprising a biocompatible and biodegradable cross-linked polymer to a further set of layers comprising a biocompatible and biodegradable cross-linked polymer, from at least one set of layers comprising a biocompatible and biodegradable cross-linked polymer to the at least one biocompatible and preferably biodegradable support layer, from the at least one biocompatible and preferably biodegradable support layer to at least one further biocompatible and preferably biodegradable support layer, etc., and combinations thereof.

According to one aspect, such a gradient is formed within or between one or more set(s) of layers comprising a biocompatible and biodegradable cross-linked polymer by altering the mechanical and/or physical properties of one or more set(s) of layers comprising a biocompatible and biodegradable cross-linked polymer. This, preferably occurs by altering (e.g. increasing or decreasing) mechanical and/or physical properties such as e.g. mechanical strength, stiffness, porosity, fiber strength, etc., within the at least one set of layers or between several sets of layers comprising a biocompatible and biodegradable cross-linked polymer, e.g. 2, 3, 4, 5, or even more sets of layers comprising a biocompatible and biodegradable cross-linked polymer. The at least one set of layers comprising a biocompatible and biodegradable cross-linked polymer preferably serves as a tissue like scaffold structure, which allows cultivation and ingrowth of cells and formation of tissue like structures or extracellular-like membranes.

According to one specific aspect, a gradient may be formed due to an alteration of the mechanical and/or physical properties within the at least one set of layers as defined above for the inventive biocompatible and preferably biodegradable gradient layer system. In this context, the gradient may be preferably formed due to an altered (e.g. increasing or decreasing) fiber strength, preferably width or diameter, of the polymer fibers in one and the same set of layers, wherein the fiber strength preferably alters from single layer to single layer. Alteration of the fiber strength, preferably the width or diameter, may be achieved by an alteration of the viscosity and/or the cross-linking ratio of the polymer used for this purpose, preferably directly prior to application or during application, e.g. by adding the crosslinker directly prior to application such that crosslinking continues during application and increases viscosity and crosslinking ratio. As an example, increasing of the fiber strength may be achieved by an increasing cross-linking ratio of the polymer used for this purpose, particularly preferable during the process of application. Likewise, increasing of the fiber strength may be achieved by an increasing viscosity of the polymer used for this purpose, particularly preferable during the process of application. Such an increasing viscosity and/or increasing cross-linking ratio of the polymer typically lead to an increasing fiber strength, preferably width or diameter, during preparation of the single layers or set of layers. Likewise, decreasing of the fiber strength may be achieved by a decreasing viscosity and/or decreasing cross-linking ratio of the polymer used for this purpose. The preparation process also may be adjusted mechanically to produce an alternating, preferably an increasing or decreasing, fiber strength during preparation of the entire set of layers.

The gradient formed by an altering, preferably increasing or decreasing, fiber strength as defined according to the present invention may correspond to an alteration, preferably increase or decrease, of the fiber strength with the height and/or number of the layer or sets of layers. Preferably, the width or diameter increases with the height and/or number of the layer or sets of layers. This alteration, preferably an increase or decrease, of the fiber strength with the height of the layer or sets of layers may occur within one layer or set of layers or even over the entire inventive biocompatible and preferably biodegradable gradient layer system with its different layers or sets of layers as defined herein. Preferably, the fiber strength, more preferably the width or diameter of the fibers, may alter, preferably increase or decrease, e.g. about 0.0001 µm-about 2 µm per µm height of the layer or set of layers, preferably about 0.0001 µm-about 1 µm per µm height of the layer or set of layers, more preferably about 0.001 µm-about 0.01 µm per µm height of the layer or set of layers, even more preferably about 0.005 µm-0.01 µm per µm height of the layer or set of layers, within one layer or set of layers or even over the entire inventive biocompatible and preferably biodegradable gradient layer system with its different layers or sets of layers as defined herein.

Alternatively or additionally, such a gradient may be defined by the preparation process of the layer or set of layers, e.g. by an increase or decrease of the fiber strength, preferably the width or diameter of the fibers, per time during said preparation. E.g. a gradient may be defined by the increase or decrease of fiber strength, preferably the width or diameter of the fibers, of the at least one set of layers during the preparation process of about 1 µm/h to about 500 nm/h, of about 100 µm/h to about 500 nm/h, of about 1 nm/h to about 500 nm/h, or of about 10 nm/h to about 500 nm/h, preferably of about 100 nm/h to about 400 nm/h, e.g. about 100, 150, 200, 250, 300, 350 or 400 nm/h, e.g. 280 nm/h.

Alternatively, a gradient may be formed by different sets of layers, each set of layers preferably comprising a biocompatible and biodegradable cross-linked polymer. In this context, the fiber strength of the polymer fibers within one and the same set of layers may remain constant within the above definition but alters with respect to the next/further set of layers, in which the polymer fibers preferably exhibit a different strength.

Preferably, the polymer fibers as defined herein, preferably of a layer or the at least one layer comprising a biocompatible and biodegradable cross-linked polymer or of a biocompatible and preferably biodegradable support layer as defined herein, may exhibit a strength, preferably a width or diameter, of between about 1 nm to about 500 µm, about 1 nm to about 250 µm, about 1 nm to about 100 µm, about 1 nm to about 50 µm, about 10 nm to about 500 µm, about 10 nm to about 250 µm, about 10 nm to about 100 µm, about 10 nm to about 50 µm, about 50 nm to about 500 µm, about 50 nm to about 250 µm, about 50 nm to about 100 µm, about 50 nm to about 50 µm.

According to the first embodiment the biocompatible and preferably biodegradable gradient layer system comprises at least one set of layers comprising a biocompatible and biodegradable cross-linked polymer. In this context, a polymer suitable as the biocompatible and biodegradable cross-linked polymer is typically selected from any polymer known to a skilled person to be biocompatible and biodegradable. Such a polymer preferably includes any naturally occurring polymer or polypeptide, preferably extracellular matrix proteins or polysaccharides. Extracellular matrix proteins are a preferred class of polypeptides suitable in this context. Examples include but are not limited to collagen, fibrin, elastin, laminin, and fibronectin, etc. Such polypeptides may be obtained from natural sources, such as from animals, preferably mammalian animals, e.g. cow, pig, sheep, etc. There are multiple types of each of these polypeptides and molecules that are naturally-occurring. Likewise, such polypeptides may be synthetically manufactured or may be produced by genetic engineering. For example, collagen occurs in many forms and types and all of these types and subsets are encompassed herein.

An especially preferred group of polypeptides suitable in this context is collagen of any type or fragments or products thereof. Collagen is a major protein component of the extracellular matrix of animals. Collagen is assembled into a complex fibrillar organization. The fibrils are assembled into bundles that form the fibers. The fibrils are made of five microfibrils placed in a staggered arrangement. Each microfibril is a collection of collagen rods. Each collagen rod is a right-handed triple-helix, each strand being itself a left-handed helix. Collagen fibrils are strengthened by covalent intra- and intermolecular cross-links which make this matrix of mature animals insoluble in cold water. Preferably, collagen within the full meaning of the term as set forth above may include full-length collagen, collagen fragments and/or analogs, collagen comprising conservative amino acid substitutions, non-conservative amino acid substitutions, and/or substitutions with non-naturally occurring amino acids or residues with respect to any type or class of collagen. The collagen used in the present invention may be derived from a natural source, may be manufactured synthetically, may be produced through genetic engineering, or may be produced through any other means or combinations thereof. Natural sources include, but are not limited to, collagens produced by or contained within the tissue of living organisms. For example, collagen used in the present invention may include, but is not limited to, autologous collagen, collagen from a conspecific organism, or collagen from another species. Some collagens that can be used include but are not limited to collagen types I, II, III, IV, V, VI, VII, VIII, IX, X, XI, XII, XIII, XIV, XV, XVI, XVII, XVIII, and XIX.

Some preferred collagens include types I and III. Synthetic collagen can include that produced by any artificial means. Numerous methods for producing collagens and other proteins are known in the art. Synthetic collagen can be prepared using specific sequences. For example, genetically engineered collagen can be prepared with specific desired sequences of amino acids that differ from natural collagen. Engineered collagen may be produced by any means, including, for example, peptide, polypeptide, or protein synthesis. For example, cells can be genetically engineered in vivo or in vitro to produce collagen or molecules capable of forming collagen, or subdomains of collagen, and the desired collagen can be harvested. In one illustrative aspect, desirable sequences that form binding sites on collagen protein for cells or peptides can be included in higher amounts than found in natural collagen. The collagen as used herein may also be formed from collagen itself or any other material that forms a collagen structure during preparation of the respective layer, formed there from. Examples include, but are not limited, to amino acids, peptides, denatured collagen such as gelatin, polypeptides, and proteins. Collagen can be formed before, during, or after preparation of the respective layer. For example, collagen may be formed by combining procollagen with procollagen peptidase before, during, or after preparation of the respective layer. When suitable treatments are used, collagen rods are extracted and solubilized where they keep their conformation as triple-helices. This is denatured collagen and differs from the native form of collagen, but has not undergone sufficient thermal or chemical treatment to break the intramolecular stabilizing covalent bonds found in collagen. When collagen solutions are extensively heated, or when the native collagen containing tissues are subjected to chemical and thermal treatments, the hydrogen and covalent bonds that stabilize the collagen helices are broken, and the molecules adopt a disordered conformation. By breaking these hydrogen bonds, the polar amine and carboxylic acid groups are now available for binding to polar groups from other sources or themselves. This material is gelatin, a form of denatured collagen, obtained by the partial hydrolysis of collagen derived from the skin, white connective tissue, or bones of animals. Gelatin may be derived from an acid-treated precursor or an alkali-treated precursor. Gelatin derived from an acid-treated precursor is known as Type A, and gelatin derived from an alkali-treated precursor is known as Type B. The macromolecular structural changes associated with collagen degradation are basically the same for chemical and partial thermal hydrolysis. In the case of thermal and acid-catalyzed degradation, hydrolytic cleavage predominates within individual collagen chains. In alkaline hydrolysis, cleavage of inter- and intramolecular cross-links predominates. Accordingly, polypeptides as used herein may also comprise gelatin selected from type-A and type-B gelatins. Collagens and gelatins prepared there from preferably have a molecular weight range of about 2,000 to about 5,000,000 Da, more preferably about 10,000 Da to about 1,000,000 Da, e.g. about 20,000 Da to about 80,000 Da, or about 30,000 Da to about 70,000 Da.

Likewise, a polymer for the biocompatible and biodegradable cross-linked polymer of the at least one set of layers of the inventive biocompatible and preferably biodegradable gradient layer system may be selected from polysaccharides, preferably including glycosaminoglycans (GAGs) or glucosaminoglycans. By glycosaminoglycan is intended any glycan (i.e., polysaccharide) comprising an unbranched (or branched) polysaccharide chain with a repeating disaccharide unit, one of which is always an amino sugar. These compounds as a class carry a high negative charge, are strongly hydrophilic, and are commonly called mucopolysaccharides. This group of polysaccharides includes heparin, heparan sulfate, chondroitin sulfate, dermatan sulfate, keratan sulfate, and hyaluronic acid. These GAGs are predominantly found on cell surfaces and in the extracellular matrix. By glucosaminoglycan is intended any glycan (i.e. polysaccharide) containing predominantly monosaccharide derivatives in which an alcoholic hydroxyl group has been replaced by an amino group or other functional group such as sulfate or phosphate. An example of a glucosaminoglycan is poly-N-acetyl glucosaminoglycan, commonly referred to as chitosan. Exemplary polysaccharides that may be useful in the present invention include dextran, heparan, heparin, hyaluronic acid, alginate, agarose, carageenan, amylopectin, amylose, glycogen, starch, cellulose, chitin, chitosan and various sulfated polysaccharides such as heparan sulfate, chondroitin sulfate, dextran sulfate, dermatan sulfate, or keratan sulfate. The polyglycan component preferably has a molecular weight range of about 2,000 to about 8,000,000 Da, more preferably about 20,000 to about 1,000,000 Da.

Preferably, the biocompatible and biodegradable cross-linked polymer is selected from collagen, gelatin, fibrin, elastin, laminin, and fibronectin, polysaccharide, glycans or polyglycans, or a combination thereof.

The biocompatible and biodegradable polymer as defined above as used for preparation of the at least one set of layers of the inventive biocompatible and preferably biodegradable gradient layer system may be cross-linked using a cross-linker. Such a cross-linker is preferably selected in dependence of the polymer to be cross-linked, preferably a polypeptide or a polysaccharide as defined above. Generally, suitable cross-linkers in the context of the present invention may comprise, without being limited thereto, anhydrides, aziridines, epoxydes, aldehydes, hexones, amino acids, such as e.g. alanine, arginine, asparagine, asparaginic acid, cysteine, glutamic acid, glutamine, glycine, histidine, isoleucine, leucine, lysine, methionin, phenylalanine, proline, serine, threonine, tryptophane, tyrosine, valine, L-leucine, L-methionine, or derivatives thereof, or any further naturally or non naturally occurring amino acid, catecholamines, such as e.g. catechol, epinephrine, noradrenaline, norepinephrine, dopamine, and any further compound carrying a catechol or 1,2-dihydroxybenzene moiety, preferably formaldehyde, dialdehydes, such as glutaraldehyde, glyoxal, glyoxal trimer dihydrate, dimethyl sub erimidate and dimethyl 3,3'-dithiobispropionimidadteglutaraldehyde, epoxides (e.g., bis-oxiranes), oxidized dextran, p-azidobenzoyl hydrazide, N-[([alpha]maleimidoacetoxy]succinimide ester, p-azidophenyl glyoxal monohydrate, bis-[[beta]-(4-azidosalicylamido) ethyl]disulfide, bis[sulfosuccinimidyl]suberate, dithiobis [succinimidyl proprionate, disuccinimidyl suberate, 1-ethyl-3-[3-dimethylaminopropyl]carbodiimide hydrochloride, diacylchlorides amino acids selected from cysteine, histidine, leucine, lysine, methionine, phenylalanine, threonine, tryptophan, tyrosine, valine, L-leucine, L-methionine, or derivatives thereof, catecholamines as defined above, and other functional cross-linking reagents known to those skilled in the art. Formaldehyde, glyoxal and glutaraldehyde react with the amino acid side chain, particularly with the lysine ε-NH$_2$ group, forming bonds similar to those in the formation of the Schiff base. Further, suitable crosslinkers, preferably with one or more polypeptides as defined herein, include but are not limited to cross-linking agents such as aldehydes e.g., glutaraldehyde, carbodiimide EDC (1-ethyl-3(3 dimethyl aminopropyl)), photosensitive materials that cross link upon exposure to specific wavelengths of light or radiation, such as UV light, selected from osmium tetroxide, carbodiimide hydrochloride, and NHS (nhydroxysuccinimide), and Factor XIIIa. Glutaraldehyde is a desirable cross-linking agent for collagen or gelatin. Alternatively, collagen or gelatin may be cross-linked by the addition of fibronectin and or heparin sulfate, or by the lysyl oxidase enzymatic cascade. Likewise preferably, polysaccharides may be cross-linked e.g. with diacylchlorides to form diester cross-links. Additionally, phenolic compounds, including monophenolic and polyphenolic compounds, preferably polyphenol compounds may be used as a crosslinker of polymers as defined herein. Such phenol compounds, preferably polyphenol compounds, are preferably selected from (i) generally moderately water-soluble compounds, (ii) having a molecular weight of about 500-4000 Da, (iii) preferably comprising >about 12 phenolic hydroxyl groups, and (iv) preferably exhibiting about 5-7 aromatic rings per 1000 Da. Specifically preferred polyphenol compounds include tannins, gallotannine (Sigma-Aldrich), compounds as defined according to the White-Bate-Smith-Swain-Haslam (WBSSH) definition, preferably proanthocyanides such as procyanidins, hydrolysable tannins and phlorotannins but also phenolic compounds, particularly phenolic compounds, which are able to complex collagen and other biomolecules, e.g. as defined in Quideau et al., Angew Chem Int Ed Engl. 2011, 50(3):586-621. Phenolic compounds also comprise e.g. curcumin, resveratrol, their related derivatives, gallic acid, chlorogenic acid, caffeic acid, carnosol, capsaicin, 6-shogaol, 6-gingerol, and their corresponding derivatives, flavonoids, flavanols, neoflavonoids, phenolic acids, etc., such as e.g. arbutin, cynarin, apigenin, isocuttelarein, luteolin, nobiletin, tangeretin, tectochrysin, galangin, kaempferol, myricetin, quercetin, rutin, citrin, curcurocitrin, eriodictyol, hesperidin, naringenin, naringin, pinocembrin, quercitrin, biochanin A, chrysin, daidzein, equol, formononetin, genistein, glycetein, ipriflavone, lactuin, lactuin, pycnogenol, silymarin, lignin, etc, or a curcumoid compound, such as curcumin, desmethoxycurcumin, bis-desmethoxycurcumin, etc., Besides covalent bonding, alternatively or additionally, also hydrogen bond formation and electrostatic interactions between the phenolic compound and the protein can occur.

The at least one set of layers comprising a biocompatible and biodegradable cross-linked polymer of the inventive biocompatible and preferably biodegradable gradient layer system may be prepared by cross-linking a suitable (biocompatible and biodegradable) polymer as defined above, preferably a (biocompatible and biodegradable) polypeptide or a polysaccharide as defined above, and forming a set of layers with the cross-linked polymer by at least one single layer, preferably one or more single layers composed to a set of layers.

Forming a set of layers comprising a biocompatible and biodegradable cross-linked polymer with the biocompatible and biodegradable cross-linked polymer may occur via any method suitable and known to a skilled person, more preferably via electroprocessing methods. In this context, the term "electroprocessing" preferably shall be defined broadly to include all methods of electrospinning, electrospraying, electroaerosoling, el ectrodeposition and electrosputtering of materials, combinations of two or more such methods, and any other method wherein polymers may be streamed, sprayed, sputtered or dripped across an electric field and toward a target. The electroprocessed biocompatible and biodegradable cross-linked polymers may be electroprocessed from one or more grounded reservoirs in the direction of a preferably charged substrate or from preferably charged reservoirs toward a grounded target. "Electrodeposition" includes any kind of depositing a biocompatible and biodegradable cross-linked polymer as defined herein via electric means on a target. For this purpose, fibers are preferably formed from a solution or melt by streaming a preferably electrically charged solution or melt through an orifice and deposited on a target. "Electrospinning" preferably means a process in which fibers are formed from a solution or melt by streaming a preferably electrically charged solution or melt through an orifice. "Electroaerosoling" preferably means a process in which droplets are formed from a solution or melt by streaming a preferably electrically charged biocompatible and biodegradable cross-linked polymer solution or melt through an orifice. The term electroprocessing is not limited to the specific examples set forth herein, and it includes any means of using an electrical field for depositing a material on a target. Preferably, forming a set of layers with the biocompatible and biodegradable cross-linked polymer may occur via electrospinning.

An electroprocessing apparatus suitable for electroprocessing biocompatible and biodegradable cross-linked polymers as defined herein via any of the above methods to at least one layer or set of layers includes an electroprocessing mechanism and a target. In preferred aspects, the electroprocessing mechanism includes one or more reservoirs to hold the one or more solutions comprising biocompatible and biodegradable cross-linked polymers as defined herein that are to be electroprocessed, e.g. electrospun or electrodeposited. The reservoir or reservoirs have at least one orifice, nozzle, or other means to allow the streaming of the solution comprising biocompatible and biodegradable cross-linked polymers as defined herein from the reservoirs. The electroprocessing typically occurs due to the presence of a charge in either the orifices or a target, while the other is grounded. The substrate can also be used as a variable feature in the electroprocessing of materials used to make the electroprocessed composition. Specifically, the target can be the actual substrate for the materials used to make electroprocessed matrix, or electroprocessed matrix itself is deposited. Alternatively, a substrate can be disposed between the target and the nozzles. The target can also be specifically charged or grounded along a preselected pattern so that the solution streamed from the orifice is directed into specific directions. The electric field can be controlled by a microprocessor to create an electroprocessed layer or set of layers comprising the biocompatible and biodegradable cross-linked polymer having a desired geometry. The target and the nozzle or nozzles can be engineered to be movable with respect to each other, thereby allowing additional control over the geometry of the electroprocessed layer or set of layers to be formed. The present invention allows forming a layer or set of layers comprising the biocompatible and biodegradable cross-linked polymer that have a predetermined shape, e.g. adapted to a specific form of e.g. a wound of a patient to be treated.

Forming a set of layers with the biocompatible and biodegradable cross-linked polymer for the inventive biocompatible and preferably biodegradable gradient layer system may occur by preparing one or more single layers step by step to form a set of layers comprising the (biodegradable and biocompatible) cross-linked polymer as defined above, preferably, wherein each new layer is formed on a preceding layer as defined above, thereby forming the set of layers.

Forming a set of layers comprising the biocompatible and biodegradable cross-linked polymer for the inventive biocompatible and preferably biodegradable gradient layer system may occur in the presence of a specific solvent. Such a solvent may be preferably already used to solubilize the biocompatible and biodegradable cross-linked polymers, or the biocompatible and biodegradable polymer as defined above and optionally a cross-linker as defined herein, prior to forming the set of layers, e.g. via electroprocessing, preferably via electrospinning. Such a solvent may be selected, without being limited thereto, from solvents useful for dissolving or suspending a polymer or polysaccharide as defined herein. Such solvents may comprise, without being limited thereto, water, ethylacetate, acetic acid, mixtures of water, ethylacetate and/or acetic acid, 2,2,2-trifluoroethanol, 1,1,1,3,3,3-hexafluoro-2-propanol (also known as hexafluoroisopropanol or HFIP), urea, acetic acid, monochloroacetic acid, trifluoroacetic acid, trifluoroacetic anhydride, lower order alcohols, such as methanol, ethanol, propanol, isopropanol, butanol, etc., halogenated alcohols, acetamide, N-methylformamide, N,N-dimethylformamide (DMF), dimethylsulfoxide (DMSO), dimethylacetamide, N-methylpyrrolidone (NMP), ethyl acetate, acetonitrile, 1,1,1-trifluoroacetone, maleic acid, hexafluoroacetone, chloroform, and trifluoroethanol (TFE) or combinations thereof. As electrospinning techniques often require more specific solvent conditions, solvents may be selected dependent on the specific polymer used, e.g. a polypeptide or polysaccharide as defined herein. For example, collagen and gelatin may be electrospun e.g. as a solution or suspension in water, ethylacetate, acetic acid, mixtures of water, ethylacetate and/or acetic acid, 2,2,2-trifluoroethanol, 1,1,1,3,3,3-hexafluoro-2-propanol (also known as hexafluoroisopropanol or HFIP), or combinations thereof. Fibrin monomer can be electrospun e.g. from solvents such as urea, monochloroacetic acid, water, 2,2,2-trifluoroethanol, HFIP, or combinations thereof. Elastin can be electrospun e.g. as a solution or suspension in water, 2,2,2-trifluoroethanol, isopropanol, HFIP, or combinations thereof, such as isopropanol and water, preferably from a solution of 70% isopropanol and 30% water containing 250 mg/ml of elastin. Preparation of a corresponding solution may occur by dissolving the at least one biocompatible and biodegradable cross-linked polymer as defined herein or the at least one biocompatible and biodegradable polymer as defined herein in a solvent as defined above, optionally in presence of a cross-linker.

Forming a set of layers comprising the biocompatible and biodegradable cross-linked polymer for the inventive biocompatible and preferably biodegradable gradient layer system may furthermore occur in form of a melt of a biocompatible and biodegradable polymer as defined herein. For this purpose, a biocompatible and biodegradable polymer as defined herein is typically heated until its melting point. The melt may contain a cross-linker as defined herein. Alternatively or additionally a set of layers comprising the biocompatible and biodegradable cross-linked polymer prepared via a melt may be crosslinked subsequent to preparation of the set of layers.

The set of layers formed with the cross-linked polymer for the inventive biocompatible and preferably biodegradable gradient layer system preferably has an ultrastructure with a three-dimensional network that supports cell adhesion and spreading, growth, proliferation, differentiation and development or migration. The spatial distance between the single fibers of the set of layers plays an important role in cells being able to obtain nutrients for growth as well as for allowing cell-cell interactions or migration to occur. Thus, according to a specific aspect of the present invention, the distance between the fibers may be about 1 nm to about 500 µm, preferably about 1 nm to about 100 µm, about 1 nm to about 500 nm, about 1 nm to about 100 nm, about 1 nm to about 50 nm, about 1 nm to about 30 nm, or even about 10 nm to about 30 nm, e.g. about 50 nm, about 100 nm, about 150 nm, about 200 nm, about 250 nm, about 300 nm, about 350 nm, about 600 nm, about 750 nm, about 800 nm, about 850 nm, about 900 nm, about 950 nm, about 1000 nm (1 µm), 10 µm), 10 µm), 50 µm), about 100 µm), about 150 µm), about 200 µm), about 250 µm), about 300 µm), about 350 µm), about 400 µm), about 450 µm), or about 500 µm). According to a preferred aspect the distance between the fibers may comprise any length between the quoted ranges or any range formed by two of any of the aforementioned values.

The pore size of the set of layers formed with the cross-linked polymer for the inventive biocompatible and preferably biodegradable gradient layer system can also be controlled through manipulation of the parameters of electrospinning. According to a specific aspect, the set of layers formed with the cross-linked polymer for the inventive biocompatible and preferably biodegradable gradient layer system has a pore size that is small enough to be impermeable to one or more types of cells. Such a pore size may be preferable for a set of layers, which can be used as an outer surface of the inventive biocompatible and preferably biodegradable gradient layer system, e.g. for protection of a wound, an organ, a specific tissue from outer impact or for infiltration of body innate tissue cells. In one aspect, the average pore diameter of the set of layers formed with the cross-linked polymer for the inventive biocompatible and preferably biodegradable gradient layer system is about 1 nm to about 500 µm, preferably about 1 nm to about 100 µm, about 1 nm to about 500 nm, about 1 nm to about 100 nm, about 1 nm to about 50 nm, about 1 nm to about 30 nm, or even about 10 nm to about 30 nm, e.g. about 500 nm or less. In another aspect, the average pore diameter of the set of layers is about 1 µm or less. In another aspect, the average pore diameter of the set of layers is about 2 µm or less. In another aspect, the average pore diameter of the set of layers is about 5 µm or less. In another aspect, the average pore diameter of the set of layers is about 8 µm or less. Some aspects have pore sizes that do not impede cell infiltration. In another aspect, the set of layers has a pore size (area) between about 1 nm$^2$ to about 500 µm$^2$, about 10 nm$^2$ to about 100 µm$^2$, about 0.1 µm$^2$ and about 100 µm$^2$, etc. In another aspect, the set of layers has a pore size (area) between about 0.1 µm$^2$ and about 50 µm$^2$. In another aspect, the set of layers has a pore size between about 1.0 µm$^2$ and about 25 µm$^2$. In another aspect, the set of layers has a pore size (area) between about 1.0 µm$^2$ and about 5 µm$^2$.

Porosity of the set of layers formed with the cross-linked polymer for the inventive biocompatible and preferably biodegradable gradient layer system can also be manipulated by mixing porogenic materials to the polymer when preparing the set of layers. Such porogenic materials may be, e.g., salts or other extractable agents, the dissolution of which will leave holes of defined sizes in the matrix. The pore size can also be controlled by the amount of cross-linking present in the matrix. Likewise, porosity of the set of layers can be manipulated by subsequent crosslinking using a crosslinker as defined above with the electroprocessed, preferably electrospun, set of layers comprising a biocompatible and biodegradable polymer as defined herein before. Furthermore, such a manipulation of the set of layers may occur via addition of e.g. polyphenol compounds and thereby, further cross-linking. Such polyphenol compounds are preferably selected from (i) generally moderately water-soluble compounds, (ii) having a molecular weight of about 500-4000

Da, (iii) preferably comprising >about 12 phenolic hydroxyl groups, and (iv) preferably exhibiting about 5-7 aromatic rings per 1000 Da. Specifically preferred polyphenol compounds include tannins, gallotannine (Sigma-Aldrich), compounds as defined according to the White-Bate-Smith-SwainHaslam (WBSSH) definition, preferably proanthocyanides such as procyanidins, hydrolysable tannins and phlorotannins but also phenolic compounds, particularly phenolic compounds, which are able to complex collagen and other biomolecules as defined e.g. in Quideau et al., Angew Chem Int Ed Engl. 2011, 50(3):586-621. Modification of the set of layers with such polyphenol compounds typically leads to a significant increase in cross-linking between the single fibers of the layer and thus to a significant improvement of mechanical strength of the layer. Such modified set(s) of layers may be used as (further) supporting means, e.g. as a protecting outer layer, etc. Modification of the set of layers may be carried out entirely or in part, e.g. edges, borderlines or further selected parts from the set of layers.

As defined above, the set of layers comprising a biocompatible and biodegradable cross-linked polymer of the inventive biocompatible and preferably biodegradable gradient layer system may be composed of one or more "single layers", i.e. the set of layers may comprise e.g. 1, 2, 3, 4, 5, 6, 7, 8, 9, 10, 1-15, 10-25, 15-30, 10-50 or 10-100 or even more "single layers". Such a layer or set of layers comprising a biocompatible and biodegradable cross-linked polymer as defined above may comprise a thickness of several nm to about several μm or even mm, preferably in the range of about 1 nm to about 5 mm, about 1 nm to about 4 mm, about 1 nm to about 3 mm, about 1 nm to about 2 mm, or about 1 nm to about 1 mm, more preferably about 10 nm to about 1 mm, about 100 nm to about 1 mm, about 1 μm to about 1 mm, about 1 μm to about 500 μm, about 1 μm to about 250 μm, about 1 μm to about 100 μm, or about 100 nm to about 100 μm, etc.

The at least one set of layers comprising a biocompatible and biodegradable cross-linked polymer as defined above may be prepared in one step or single layer by single layer in a continuous mode. Furthermore, if more than one set of layers is prepared comprising a biocompatible and biodegradable cross-linked polymer as defined above, each set of layers is preferably as defined herein for the set of layers comprising a biocompatible and biodegradable cross-linked polymer as defined above. If more than one set of layers comprising a biocompatible and biodegradable cross-linked polymer as defined above is prepared, each set of layers may be prepared separately or in a continuous mode subsequent to each other. A set of layers as defined herein may be prepared on a suitable support, an already prepared set of layers comprising a biocompatible and biodegradable cross-linked polymer as defined above, on at least one biocompatible and preferably biodegradable support layer as defined herein, etc., or any surface or support suitable for this purpose, e.g. a steel plate, paper, glass, a glass slide or any object holder, a petri-dish, a Teflon surface, e.g. a Teflon foil, a parafilm, an aluminium plate, an aluminium foil, plastic foil, etc. In this context, the support or surface may be a form or a mold, which resembles the 3D-structure of a tissue fragment to be reconstituted, etc.

If more than one set of layers comprising a biocompatible and biodegradable cross-linked polymer as defined above is prepared, a first set of layers may be prepared on a support as defined above. Subsequent to preparation of such a first set of layers, a second set of layers may be prepared, wherein such a second set of layers may be prepared likewise on a support as defined above, or may be prepared on the first set of layers to obtain a staggered structure of two sets of layers.

Such sets of layers comprising a biocompatible and biodegradable cross-linked polymer, preferably in a staggered structure as defined above, may be orientated to each other in each suitable orientation. As an example, if two sets of layer are prepared, the side of the second set of layers exhibiting a larger porosity, larger fiber lengths and/or smaller fiber strengths may be placed on the side of the first set of layers exhibiting a smaller porosity, smaller fiber lengths and/or larger fiber strengths. Likewise, the side of the second set of layers exhibiting a smaller porosity, smaller fiber lengths and/or larger fiber strengths may be placed on the side of the first set of layers exhibiting a larger porosity, larger fiber lengths and/or smaller fiber strengths, preferably regarding the width or diameter of the fibers. Alternatively, the side of the second set of layers exhibiting a smaller porosity, smaller fiber lengths and/or larger fiber strengths may be placed on the side of the first set of layers exhibiting a smaller porosity, smaller fiber lengths and/or larger fiber strengths. Likewise, the side of the second set of layers exhibiting a larger porosity, larger fiber lengths and/or smaller fiber strengths may be placed on the side of the first set of layers exhibiting a larger porosity, larger fiber lengths and/or smaller fiber strengths.

Further sets of layers comprising a biocompatible and biodegradable cross-linked polymer as defined above may be prepared following the same principle as defined above for preparation of a staggered structure of such sets of layers. As an example, further sets of layers comprising a biocompatible and biodegradable cross-linked polymer as defined above may be prepared accordingly on a subsequent set of layers to form a staggered set of layers comprising, e.g. 1, 2, 3, 4, 5, 6, 7, 8, 9 or even 10 or more different sets of layers as described herein, wherein each set of layers may be orientated to the subsequent layer as described before exemplarily for a first and a second set of layers. As an example, all sets of layers may comprise the same orientation, i.e. either the side of one set of layers exhibiting a larger porosity, larger fiber lengths and/or smaller fiber strengths may be placed on the side of a further set of layers exhibiting a smaller porosity, smaller fiber lengths and/or larger fiber strengths. Likewise, the side of one set of layers exhibiting a smaller porosity, smaller fiber lengths and/or larger fiber strengths may be placed on the side of a further set of layers exhibiting a larger porosity, larger fiber lengths and/or smaller fiber strengths.

Such different sets of layers comprising a biocompatible and biodegradable cross-linked polymer as defined above may be prepared using the same or different of the above defined biocompatible and biodegradable cross-linked polymers in the different sets of layers, e.g. about 1, 2, 3, 4, or even 5 or more different of the above defined biocompatible and biodegradable cross-linked polymers. Without being limited thereto, particularly preferred combinations include gelatin an elastin.

Furthermore, a set of layers as defined above comprising a biocompatible and biodegradable cross-linked polymer as defined above may be prepared using one or more than one biocompatible and biodegradable cross-linked polymer as defined above in each set of layers, e.g. 2, 3, 4, or even 5 or more different biocompatible and biodegradable cross-linked polymers as defined above. Preparation of such a set of layers may occur via any method as defined above, preferably via electroprocessing, such as e.g. electrospinning or electrodeposition, more preferably via co-spinning, i.e. electrospinning as defined above, wherein the single layers are prepared using different biocompatible and biodegradable cross-linked polymers as defined above at the same time (e.g. using separate nozzles for each of the polymers). Any of the definitions of the sets of layers as defined above may also apply here, particularly with respect to strength of the polymeric fibers and alteration of the mechanical and/or physical properties of the set of layers, but also with respect to the modification of the set of layers, the orientation of different sets of layers to each other, etc.

According to a very specific aspect a set of layers as defined above comprising a biocompatible and biodegradable cross-linked polymer as defined above may be prepared using following steps:
(i) providing and preparing a polymer solution for electroprocessing, preferably by dissolving a biocompatible and biodegradable cross-linked polymer as defined herein, preferably in a solvent as defined herein, optionally in the presence of a cross-linker as defined herein, by dissolving a biocompatible and biodegradable polymer as defined herein and a cross-linker as defined herein, preferably in a solvent as defined herein, or by melting a biocompatible and biodegradable polymer as defined herein, optionally in the presence of a cross-linker as defined herein; and
(ii) electroprocessing at least one set of layers from the polymer solution, thereby forming a 3-dimensional set of layers, wherein a gradient is formed as defined herein, preferably by altering the strength of the fibers of the set of layers as defined herein, more preferably increasing or decreasing, while carrying out the electroprocessing process; and optionally molding the produced set of layers. If a solvent was used, the solvent is preferably volatilized in step (ii) during the step of electroprocessing the polymer solution.

The at least one set of layers comprising a biocompatible and biodegradable cross-linked polymer of the inventive biocompatible and preferably biodegradable gradient layer system may have any suitable form. Suitable forms comprise, without being limited thereto, bands, strands, fleeces, fibers, particles, drops, or net or mesh-like structures. Suitable forms may also comprise sheets, films, foils, or laminates. Preferably, the at least one layer comprising a biodegradable and biocompatible cross-linked polymer of the inventive biocompatible and preferably biodegradable gradient layer system is present in form of a fleece, a net or a mesh-like structure. Any of these structures may occur with or without holes or cavities.

As a further component, the biocompatible and preferably biodegradable gradient layer system according to the first embodiment of the present invention comprises at least one biocompatible and preferably biodegradable support layer. Such a biocompatible and preferably biodegradable support layer may comprise a biocompatible and preferably biodegradable meltable polymer and/or an incorporable material. Biodegradable and preferably biocompatible meltable polymers in this context may include, without being limited thereto, any biocompatible and preferably biodegradable meltable polymer suitable for such a purpose, preferably e.g. polyesters, polyanhydrides, polypeptides or polyurethanes e.g. polycaprolactone PCL, preferably poly(epsilon-caprolactone) (PCL), polylactide PLA, polyglycolide PGA, poly (lactic-co-glycolic) acid PLGA, polysebacic acid, etc., or biopolymers such as e.g. gelatin, alginate, collagen, fibrin etc. Biocompatible and incorporable materials in this context may include, without being limited thereto, any biocompatible and incorporable material suitable for such a purpose, preferably e.g. ceramics, such as e.g. ceramics made from hydroxyl apatite (HA), tricalcium phospate (TCP), etc. A biocompatible and preferably biodegradable support layer as defined herein may also comprise a biocompatible and preferably biodegradable meltable polymer as defined herein containing an incorporable material as defined herein. Such a biocompatible and preferably biodegradable support layer preferably acts as a binder and/or as a structural support to create a mechanically stable biocomposite material. Depending on the desired application, such biocompatible incorporable materials can be used as stiff support for e.g. hard tissue supplementation or regeneration, bone repair, etc.

In this context, the term "meltable" preferably means, that the biodegradable and biocompatible meltable polymer comprises a solid state or semi-solid state at room temperature of about 20 to 25° C. and/or at the regular body temperature of patient to be treated, e.g. of about 37° C. Accordingly, a biodegradable and biocompatible meltable polymer as defined herein may be selected with respect to its melting point and glass transition temperature. If the biodegradable and biocompatible meltable polymer used as a support layer herein is to be flexible, the glass transition temperature of such a polymer may be selected such that the polymer is at the regular body temperature of patient to be treated above its glass transition point $T_g$. This allows for movement of the polymeric chains against each other and therefore provide for a certain flexibility. Additionally, the polymer is preferably selected such that its melting point is above the room temperature of about 20 to 25° C. and/or at the regular body temperature of patient to be treated, e.g. of about 37° C. As an example, the melting point of PCL is about 60° C. and its glass transition temperature $T_g$ is about −60° C.

The at least one biocompatible and preferably biodegradable support layer of the inventive biocompatible and preferably biodegradable gradient layer system according to the first embodiment may be prepared by firstly providing a melt of the biocompatible and preferably biodegradable meltable polymer. Alternatively, a suspension or solution of an incorporable material as defined above may be provided, e.g. in a solvent as defined herein, preferably in polyvinylalcohol (PVA). According to a further alternative, a melt of the biocompatible and preferably biodegradable meltable polymer may be provided, further comprising an incorporable material as defined above. Preparation of the at least one layer comprising a biocompatible and preferably biodegradable support layer of the inventive biocompatible and preferably biodegradable gradient layer system may then occur by forming a layer with the molten polymer, with the suspension or solution of an incorporable material as defined above, and/or with a melt of the biodegradable meltable polymer may be provided, further comprising an incorporable material as defined above.

Forming at least one biocompatible and preferably biodegradable support layer with the molten polymer, with the suspension or solution of an incorporable material as defined above, and/or with a melt of the biodegradable meltable polymer, optionally further comprising an incorporable material as defined above in the context of the inventive biocompatible and preferably biodegradable gradient layer system may occur via any method known to a skilled person. Such methods may comprise any of the electroprocessing methods as defined above, preferably methods of electrospinning, electrospraying, electroaerosoling, electrodepositing and electrosputtering of materials, combinations of two or more such methods, and any other method wherein polymers may be streamed, sprayed, sputtered or dripped across an electric field and toward a target. The electroprocessed polyesters may be electroprocessed from one or more grounded reservoirs in the direction of a preferably charged substrate or from preferably charged reservoirs toward a grounded target.

Alternatively and more preferably, forming at least one biocompatible and preferably biodegradable support layer with the molten polymer, with the suspension or solution of an incorporable material as defined above, and/or with a melt of the biodegradable meltable polymer, optionally further comprising an incorporable material as defined above in the context of the inventive biocompatible and preferably biodegradable gradient layer system may occur via Rapid Prototyping Techniques, preferably via 3D-Plotting, e.g. using a 3D-Plotter (e.g. 3D-BioPlotter from the company Envisiontec). In this context, rapid prototyping is preferably to be understood as an automatic construction of physical objects using additive manufacturing technology. Such a technology typically utilizes additive manufacturing of a meltable polymer for rapid prototyping of virtual designs from computer aided design (CAD) or animation modeling software, transforms them into thin, virtual, horizontal cross-sections and then creates successive layers until the model is complete.

According to a particularly preferred aspect, the at least one biocompatible and preferably biodegradable support layer may be formed from a molten polymer, with the suspension or solution of an incorporable material as defined above, and/or with a melt of the biodegradable meltable polymer, optionally further comprising an incorporable material as described herein, preferably using a 3D-Plotter. 3D-Plotting may occur e.g. by melting the polymer or preparing a suspension or solution of an incorporable material as defined herein, and providing the molten polymer or the suspension or solution onto a surface, e.g. via a dispenser of a 3D Plotter, which forms a desired single layer upon movement of the dispenser. The dispenser usually presses or pumps the molten polymer or suspension or solution through a nozzle of the dispenser onto a surface as defined herein, e.g. via air pressure. Preferably, the dispenser may be moved into any desired direction (up, down, left, right, forward, backward), preferably with an adjustable speed, to form a desired structure. During movement of the dispenser, the molten polymer or suspension or solution is preferably pressed out through the nozzle and provides e.g. fibers, bands, dots, etc., or whatever form is desired or obtained, preferably due to the form of the nozzle. Upon forming fibers, bands, dots, etc., preferably a predetermined 3D-structure is formed. Such a 3D-structure may comprise a single layer of the polymer or the incorporable material or may be composed of several single layers of the polymer or the incorporable material as already disclosed herein. Such single layers may also form a set of layers as already defined above for the at least one set of layers comprising a biocompatible and preferably biodegradable cross-linked polymer. Such a set of layers may be composed of one or more "single layers", i.e. the set of layers may comprise e.g. 1, 2, 3, 4, 5, 6, 7, 8, 9, 10, 1-15, 10-25, 15-30, 10-50 or 10-100 or even more "single layers" of the polymer or the incorporable material. Such a layer or set of layers of the polymer or the incorporable material may comprise a thickness of several nm to about several µm or even mm, preferably in the range of about 100 nm to about 5 mm, about 100 nm to about 4 mm, about 100 nm to about 3 mm, about 100 nm to about 2 mm, or about 100 nm to about 1 mm, more preferably about 1 µm to about 2 mm, about 1 µm to about 1 mm, about 1 µm to about 500 µm, about 1 µm to about 250 µm, about 10 µm to about 250 µm, or about 10 µm to about 100 µm, etc.

During 3D-Plotting, the temperature may be adjusted as suitable. If a biocompatible and preferably biodegradable meltable polymer, optionally supplemented with an incorporable material as defined herein, is used, 3-D Plotting is typically carried out at a temperature, at which the biocompatible and preferably biodegradable meltable polymer as defined herein is present in a molten form, wherein the temperature is typically adjusted to keep the polymer molten until extrusion via a nozzle or needle. Likewise, if a suspension or solution of an incorporable material as defined above is used, typically no elevated temperature needs to be applied. Accordingly, the application and working temperatures are typically selected in dependence on the specific requirements of each biocompatible and preferably biodegradable meltable polymer or incorporable material as defined herein. The temperatures may be adjusted using e.g. a high temperature- or a low temperaturehead/module for application of the molten polymer and/or the suspension or solution of an incorporable material as defined above. The low temperature head/module may likewise be cooled (e.g. <0° C.), whereas the high temperature head/module may be heated until the desired temperature, e.g. until 50° C., 100° C., 150° C., 200° C. or even 250° C. or even more. The nozzle or needle may be moved e.g. with a driver speed of about 1 to about 1000 mm/minute. The resolution of x/y/z axis may be about 0.05 mm, e.g. between about 10 µm to about 1 mm. The applied pressure for extrusion of the molten polymer or the suspension or solution may be about 0 to about 5 bar.

Forming at least one biocompatible and preferably biodegradable support layer with the molten polymer, with the suspension or solution of an incorporable material as defined above, and/or with a melt of the biodegradable meltable polymer, optionally further comprising an incorporable material as defined above in the context of the inventive biocompatible and preferably biodegradable gradient layer system may occur on any suitable support, an already prepared set of layers comprising a biocompatible and biodegradable cross-linked polymer as defined above, on at least one biocompatible and preferably biodegradable support layer as defined herein, etc., or any surface or support suitable for this purpose, e.g. a steel plate, paper, glass, a glass slide or any object holder, a Petri dish, a Teflon surface, e.g. a Teflon foil, a parafilm, an aluminium plate, an aluminium foil, plastic foil, etc. In this context, the support or surface may be a form or a mold, which resembles the 3D-structure of a tissue fragment to be reconstituted, etc. 3D-Plotting of molten polymers is preferably carried out on a Teflon foil, since the plotted polymer/support layer may be released easily from this surface.

The form and thickness of the layer(s) of the biocompatible and preferably biodegradable support layer furthermore may be adjusted as suitable, preferably as already described herein for the at least one set of layers comprising a biocompatible and preferably biodegradable cross-linked polymer. Particularly, any of such parameters, e.g. distance between the fibers, if fibers are produced, pore size, thickness, etc. may be applied to the support layer or set of layers as already discussed above for the at least one set of layers comprising a biocompatible and preferably biodegradable cross-linked polymer.

According to a further particularly preferred aspect, the at least one biocompatible and preferably biodegradable support layer may be formed using a biocompatible incorporable material as defined above. For this purpose, the biocompatible incorporable material is preferably solved or suspended in a solvent and provided on a surface to form a predetermined 3D-structure. According to an example, an hydroxyapatite ceramic support layer may be formed by solving polyvinylalkohol (PVA) (10% (weight), Mowiol 28-99, Clariant GmbH, Frankfurt a.M., Deutschland) in hot aqua dest. The thus obtained solution/suspension (e.g. 2 parts) may then be mixed with hydroxylapatite (e.g. 1 part, e.g. Typ SF microfine powder C13-09, Chemische Fabrik Budenheim, Mainz, Germany). The mixture is then preferably sieved to remove clots or cluster (100 µm, Retsch, Haan, Germany). The mixture is then preferably applied on a surface as defined above using a 3D-Plotter (Envisiontec, Gladbeck, Germany). Processing temperature may be about room temperature. The support structure may have e.g. a form as defined herein, e.g. a net or mesh-like structure. The support structure may be stored until use, e.g. in frozen form. Freezing preferably occurs immediately subsequent to preparation of the support structure, e.g. at about −30° C. initially, preferably reducing the temperature to about −200° C. and freeze drying the support structure (e.g. in a Lyovac GT 2, Amsco/Finn-Aqua, Hürth, Germany). In order to remove polyvinylalkohol (PVA) from the support structure, the support structure are preferably sintered or baked (e.g. about 5 h (about 2 to about 10 h), about 350° C. (about 200° C. to about 600° C.)) at least once. In a further step, the support structure may be sintered again (e.g. about 12 h (about 5 to about 20 h), about 1100° C. (about 500° C. to about 2000° C.)), which preferably leads to sintering of the hydroxyl apatite particles to a ceramic support layer.

The at least one biocompatible and preferably biodegradable support layer may be stored, freezedried, sterilized, plasma sterilized, etc., prior to use with a further at least one biocompatible and preferably biodegradable support layer or a biodegradable and biocompatible meltable polymer or incorporable material of the inventive biocompatible and preferably biodegradable gradient layer system.

The at least one biocompatible and preferably biodegradable support layer of the inventive biocompatible and preferably biodegradable gradient layer system may have any suitable form. Suitable forms comprise, without being limited thereto, bands, strands, fleeces, fibers, particles, drops, or net or mesh-like structures. Suitable forms may also comprise sheets, films, foils or laminates. Preferably, the at least one biocompatible and preferably biodegradable support layer of the inventive biocompatible and preferably biodegradable gradient layer system is in the form of bands, strands, a fleece, fibers, particles, drops, a net or a mesh-like structure, a sheet, a film, a foil, or a laminate. Any of these structures may occur with or without holes or cavities.

Preparation of the at least one biocompatible and preferably biodegradable support layer of the inventive biocompatible and preferably biodegradable gradient layer system may occur separately and independent of the preparation of the at least one set of layers comprising a biocompatible and biodegradable cross-linked polymer as defined above.

According to a very specific aspect the at least one biocompatible and preferably biodegradable support layer as defined herein may be prepared using following steps:
(i) providing a molten biocompatible and preferably biodegradable meltable polymer as defined herein, a suspension or solution of a biocompatible incorporable material as defined herein, and/or a melt of a biocompatible and preferably biodegradable meltable polymer, optionally further comprising a biocompatible incorporable material as defined herein; and
(ii) electroprocessing or 3D-Plotting, the molten biocompatible and preferably biodegradable meltable polymer as defined herein, a suspension or solution of a biocompatible incorporable material as defined herein, and/or a melt of a biocompatible and preferably biodegradable meltable polymer, optionally further comprising a biocompatible incorporable material as defined herein on a surface as defined herein.

In the inventive biocompatible and preferably biodegradable gradient layer system the at least one set of layers comprising a biocompatible and preferably biodegradable cross-linked polymer and the at least one biocompatible and preferably biodegradable support layer as defined herein may be arranged together to form the inventive biocompatible and preferably biodegradable gradient layer system. Such an arrangement may comprise any number of the layers or sets of layers of any kind as defined herein and as suitable for a specific purpose.

For example, the inventive biocompatible and preferably biodegradable gradient layer system may be formed by providing as a first element at least one set of layers (e.g. 1, 2, 3, 4, 5 or even more sets of layers) each set off layers comprising the same or a different biocompatible and biodegradable cross-linked polymer as defined herein, and applying as a second element at least one biocompatible and preferably biodegradable support layer or set of layers as defined herein on this first element.

Likewise, the inventive biocompatible and preferably biodegradable gradient layer system may be formed by providing as a first element at least one set of layers comprising the same or a different biocompatible and biodegradable cross-linked polymer as defined herein, by applying as a second element at least one biocompatible and preferably biodegradable support layer or set of layers as defined herein on this first element, and by applying as a third element again at least one set of layers comprising the same or a different biocompatible and biodegradable cross-linked polymer as defined herein on the second element. The orientation of the layers may be as suitable, e.g. the first and the third set of layers may be oriented to each other in the same direction or vice versa. Likewise, the second layer or set of layers may be oriented to the first or the third set of layers in the same direction or vice versa.

According to a very specific aspect the inventive biocompatible and preferably biodegradable gradient layer system may be prepared using following steps:
(i) optionally providing and preparing a polymer solution for electroprocessing, preferably by dissolving a biocompatible and biodegradable cross-linked polymer as defined herein, preferably in a solvent as defined herein, optionally in the presence of a cross-linker as defined herein, by dissolving a biocompatible and biodegradable polymer as defined herein and a cross-linker as defined herein, preferably in a solvent as defined herein, or by melting a biocompatible and biodegradable as defined herein, optionally in the presence of a cross-linker as defined herein;
(ii) optionally electroprocessing at least one set of layers from the polymer solution, thereby forming a 3-dimensional set of layers, wherein a gradient is formed as defined herein, preferably by altering the strength of the fibers of the set of layers as defined herein, more preferably increasing or decreasing, while carrying out the electroprocessing process; and optionally molding the produced set of layers. If a solvent was used, the solvent is preferably volatilized in step (ii) during the step of electroprocessing the polymer solution;

(iii) providing a molten biocompatible and preferably biodegradable meltable polymer as defined herein, a suspension or solution of a biocompatible incorporable material as defined herein, and/or a melt of a biocompatible and preferably biodegradable meltable polymer, optionally further comprising a biocompatible incorporable material as defined herein;

(iv) electroprocessing or 3D-Plotting, the molten biocompatible and preferably biodegradable meltable polymer as defined herein, a suspension or solution of a biocompatible incorporable material as defined herein, and/or a melt of a biocompatible and preferably biodegradable meltable polymer, optionally further comprising a biocompatible incorporable material as defined herein on a surface as defined herein;

(v) optionally providing and preparing a polymer solution for electroprocessing, preferably by dissolving a biocompatible and biodegradable cross-linked polymer as defined herein, preferably in a solvent as defined herein, optionally in the presence of a cross-linker as defined herein, by dissolving a biocompatible and biodegradable polymer as defined herein and a cross-linker as defined herein, preferably in a solvent as defined herein, or by melting a biocompatible and biodegradable as defined herein, optionally in the presence of a cross-linker as defined herein; and (vi) optionally electroprocessing at least one set of layers from the polymer solution, thereby forming a 3-dimensional set of layers, wherein a gradient is formed as defined herein, preferably by altering the strength of the fibers of the set of layers as defined herein, more preferably increasing or decreasing, while carrying out the electroprocessing process; and optionally molding the produced set of layers. If a solvent was used, the solvent is preferably volatilized in step (ii) during the step of electroprocessing the polymer solution.

Subsequent to preparation of the inventive biocompatible and preferably biodegradable gradient layer system as described above, the gradient layer system is preferably washed at least once, twice or even more (3, 4, or 5 times or more), preferably with water, a buffer, such as a buffer used for culturing the cells described herein, etc.

The inventive biocompatible and preferably biodegradable gradient layer system as described above may also be supplemented by a further set of layers comprising a biocompatible and biodegradable polymer as defined herein and/or by a further at least one biocompatible and preferably biodegradable support layer, wherein the at least one layer or set of layers has been modified with a polyphenol compound as defined above.

Any further form of the inventive biocompatible and preferably biodegradable gradient layer system may be realized. Precisely, any of the different layers and/or sets of layers, particularly any of the at least one set of layers comprising a biocompatible and preferably biodegradable cross-linked polymer and/or any of the at least one biocompatible and preferably biodegradable support layer may be contained in the inventive biocompatible and preferably biodegradable gradient layer system in any number and any orientation. Thus, it is to be noted that the inventive biocompatible and preferably biodegradable gradient layer system is not restricted to any specific arrangement of layers or sets of layers.

The inventive biocompatible and preferably biodegradable gradient layer system may furthermore comprise cells. Such cells preferably comprise, but are not limited to, (mammalian, human or nonhuman) stem cells selected from, committed stem cells, differentiated cells, adult stem cells, embryonic stem cells, bone marrow stem cells and umbilical cord stem cells, engineered or non-engineered stem cells, primary or immortalized (cell-line) stem cells, preferably mesenchymal stem cells. Other examples of cells used in various aspects include, but are not limited to, cartilage cells, epithelial cells, endothelial cells, endothelial cells of vascular and corneal tissue, skin cells, osteocytes, osteoblasts, cementoblasts, bone cells, myoblasts, neuroblasts, fibroblasts cells of all connective tissues, gingival and/or skin and corneal fibroblasts, either alone or together with periodontal ligament fibroblasts, keratinocytes, e.g. gingival keratinocytes and keratinocytes from the oral cavity and upper aerodigestive tract, as well as from the skin and the ocular surface, glioblasts, germ cells, hepatocytes, chondrocytes, smooth muscle cells, cardiac muscle cells, connective tissue cells, glial cells, hormone-secreting cells, cells of the immune system, and neurons, but also e.g. cells of the central nervous system, neuronal cells, pericytes, myocytes, adipocytes, astrocytes, melanocytes, etc. In some aspects it is unnecessary to pre-select the type of stem cell that is to be used, because many types of stem cells can be induced to differentiate in an organ specific pattern once delivered to a given organ. For example, a stem cell delivered to the liver can be induced to become a liver cell simply by placing the stem cell within the liver. Cells in the matrix can serve the purpose of providing scaffolding or seeding, producing certain compounds, or both. Cells in the above meaning may also comprise viable tissue cells for certain therapeutic uses. It is preferable, but not required, that the tissue cells originate from the same type of tissue for which the inventive biocompatible and preferably biodegradable gradient layer system will be used therapeutically. The viable tissue cells can be derived from autologous tissue sources, allogenic tissue sources, or xenogenic tissue sources. The term "autologous" is meant to refer to tissue that originates from the same host. The term "allogenic" is meant to refer to tissue that originates from a source that is of the same species (i.e., human) but of non-identical genetic composition. The term "xenogenic" is meant to refer to tissue that originates from a species different from the host. Non-limiting examples of types of cells that can be used in combination with the inventive biocompatible and preferably biodegradable gradient layer system include stem cells, bone cells, tenocytes, adipocytes, cardiomyocytes, hepatocytes, smooth muscle cells, endothelial cells, and the like. The tissue cells can be added to the inventive biocompatible and preferably biodegradable gradient layer system prior to, during, or after cross-linking occurs. Cells as used herein may also comprise a mixture of cells as defined before.

The cells as defined above are preferably cultivated with the inventive biocompatible and preferably biodegradable gradient layer system as defined herein, e.g. in a culture medium suitable for the specific type of cells. Cells can also be placed in a lumen or space within a construct, or implanted adjacent to the inventive biocompatible and preferably biodegradable gradient layer system to facilitate growth. Alternatively, the inventive biocompatible and preferably biodegradable gradient layer system can be placed in a bioreactor. There are several kinds of commercially available bioreactors, devices designed to provide a low-shear, high nutrient perfusion environment. Until recently, most of the available bioreactors maintained cells in suspension and delivered nutrients and oxygen by sparging, through the use of impellers, or other means of stirring.

The inventive biocompatible and preferably biodegradable gradient layer system may also comprise cells that can be cultured in vitro, derived from a natural source, genetically engineered, or produced by any other means. Any natural source of prokaryotic or eukaryotic cells may be used, e.g. cells as defined above. Aspects in which the inventive biocompatible and preferably biodegradable gradient layer system is implanted in an organism can use cells from the recipient, cells from a conspecific donor or a donor from a different species, or bacteria or microbial cells. Cells harvested from a source and cultured prior to use are included.

According to one particular aspect, cells as contained in the inventive biocompatible and preferably biodegradable gradient layer system may contain cells that have been genetically engineered. The engineering involves programming the cell to express one or more genes, repressing the expression of one or more genes, or both. One example of genetically engineered cells useful in the present invention is a genetically engineered cell that makes and secretes one or more desired molecules. When the inventive biocompatible and preferably biodegradable gradient layer system comprises genetically engineered cells and is implanted or transplanted in an organism, the molecules produced can produce a local effect or a systemic effect, and can include the molecules identified above as possible substances. Cells can also produce antigenic materials in aspects in which one of the purposes of the inventive biocompatible and preferably biodegradable gradient layer system is to produce an immune response. Cells may produce substances to aid in the following non-inclusive list of purposes: inhibit or stimulate inflammation; facilitate healing; resist immunorejection; provide hormone replacement; replace neurotransmitters; inhibit or destroy cancer cells; promote cell growth; inhibit or stimulate formation of blood vessels; augment tissue; and to supplement or replace neurons, skin, epithelia in general, synovial fluid, tendons, cartilage, ligaments, bone, muscle, organs, dura, blood vessels, bone marrow, and extracellular matrix. Genetic engineering can involve, for example, adding or removing genetic material to or from a cell, altering existing genetic material, or both. Aspects in which cells are transfected or otherwise engineered to express a gene can use transiently or permanently transfected genes, or both. Gene sequences may be full or partial length, cloned or naturally occurring.

It is to be understood that the inventive biocompatible and preferably biodegradable gradient layer system may be combined or supplemented with other materials and/or substances. For example, an inventive biocompatible and preferably biodegradable gradient layer system may be combined or supplemented with an adjuvant to enhance immunogenicity when implanted subcutaneously. Likewise, an inventive biocompatible and preferably biodegradable gradient layer system may be combined or supplemented with a pharmaceutical agent. As another example, an inventive biocompatible and preferably biodegradable gradient layer system, containing cells, may be combined or supplemented with e.g. interleukins and/or growth factors to stimulate growth and division of the cells in the gradient layer system.

According to one aspect, the inventive biocompatible and preferably biodegradable gradient layer system may comprise a pharmaceutical agent. Pharmaceutical agents suitable herein can be organic or inorganic and may be in a solid, semisolid, liquid, or gas phase. Molecules may be present in combinations or mixtures with other molecules, and may be in solution, suspension, or any other form. Examples of classes of molecules that may be used include human or veterinary therapeutics, cosmetics, nutraceuticals, agriculturals such as herbicides, pesticides and fertilizers, vitamins, salts, electrolytes, amino acids, peptides, polypeptides, proteins, carbohydrates, lipids, nucleic acids, glycoproteins, lipoproteins, glycolipids, glycosaminoglycans, proteoglycans, growth factors, hormones, neurotransmitters, pheromones, chalones, prostaglandins, immunoglobulins, monokines and other cytokines, humectants, metals, gases, minerals, plasticizers, ions, electrically and magnetically reactive materials, light sensitive materials, anti-oxidants, phenolic compounds, monophenolic compounds or polyphenolic compounds, preferably as defined above, e.g. curcumin, resveratrol, their related derivatives, gallic acid, chlorogenic acid, caffeic acid, carnosol, capsaicin, 6-shogaol, 6-gingerol, and their corresponding derivatives, flavonoids, flavanols, neoflavonoids, phenolic acids, etc., such as e.g. arbutin, cynarin, apigenin, isocuttelarein, luteolin, nobiletin, tangeretin, tectochrysin, galangin, kaempferol, myricetin, quercetin, rutin, citrin, curcurocitrin, eriodictyol, hesperidin, naringenin, naringin, pinocembrin, quercitrin, biochanin A, chrysin, daidzein, equol, formononetin, genistein, glycetein, ipriflavone, lactuin, lactuin, pycnogenol, silymarin, lignin, etc, or a curcumoid compound, such as curcumin, desmethoxycurcumin, bis-desmethoxycurcumin, etc., catecholamins, or catecholamines, such as e.g. catechol, epinephrine, noradrenaline, norepinephrine, dopamine, and any further compound carrying a catechol or 1,2-dihydroxybenzene moiety, molecules that may be metabolized as a source of cellular energy, antigens, and any molecules that can cause a cellular or physiological response. Any combination of molecules can be used, as well as agonists or antagonists of these molecules.

Pharmaceutical agents may furthermore include any therapeutic molecule or substance including, without limitation, any pharmaceutical substance or drug. Examples of pharmaceuticals include, but are not limited to, anaesthetics, hypnotics, sedatives and sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmodics, appetite suppressants, neuroactive substances, neurotransmitter agonists, antagonists, receptor blockers and reuptake modulators, beta-adrenergic blockers, calcium channel blockers, disulfuram and disulfuram-like drugs, muscle relaxants, analgesics, antipyretics, stimulants, anti-cholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, vitamins, cosmetics, anti-inflammatories, wound care products, antithrombogenic agents, antitumoral agents, antiangiogenic agents, anesthetics, antigenic agents, wound healing agents, plant extracts, growth factors, emollients, humectants, rejection/anti-rejection drugs, spermicides, conditioners, antibacterial agents, antifungal agents, antiviral agents, antibiotics, tranquilizers, cholesterol-reducing drugs, antitussives, histamine-blocking drugs, monoamine oxidase inhibitor. All substances listed by the U.S. Pharmacopeia are also included within the substances of the present invention.

The inventive biocompatible and preferably biodegradable gradient layer system may further include therapeutic substances, selected from, but are not limited to, antineoplastic, antimitotic, antiinflammatory, antiplatelet, anticoagulant, antifibrin, antithrombin, antiproliferative, antibiotic, antioxidant, and antiallergic substances as well as combinations thereof. Examples of such antineoplastics and/or antimitotics include paclitaxel (e.g., TAXOL® by Bristol-Myers Squibb Co., Stamford, Conn.), docetaxel (e.g., Taxotere® from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-proargchloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibi tors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoAreductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostagiandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents that may be used include alpha-interferon, genetically engineered epithelial cells, and dexamethasone. In other examples, the therapeutic substance is a radioactive isotope for incorporable device usage in radiotherapeutic procedures. Examples of radioactive isotopes include, but are not limited to, phosphoric acid ($H_3P^{32}O_4$), palladium ($Pd^{103}$), cesium ($CS^{131}$), and iodine ($I^{125}$).

Furthermore, the inventive biocompatible and preferably biodegradable gradient layer system may be cultivated with or may be supplemented with other components or substances. Such components or substances may include, e.g., any molecule, for example, organic or inorganic, in a solid, semisolid, liquid, or gas phase. Molecules may be present in combinations or mixtures with other molecules, and may be in solution, suspension, or any other form. Examples of classes of molecules that may be used include human or veterinary therapeutics, nutraceuticals, vitamins, salts, electrolytes, amino acids, peptides, polypeptides, proteins, carbohydrates, lipids, nucleic acids, glycoproteins, lipoproteins, glycolipids, glycosaminoglycans, proteoglycans, growth factors, hormones, neurotransmitters, pheromones, chalones, prostaglandins, immunoglobulins, monokines and other cytokines, humectants, metals, gases, minerals, plasticizers, ions, electrically and magnetically reactive materials, light sensitive materials, anti-oxidants, molecules that may be metabolized as a source of cellular energy, antigens, and any molecules that can cause a cellular or physiological response. Any combination of molecules can be used, as well as agonists or antagonists of these molecules.

Other preferred components, which may be contained in the inventive biocompatible and preferably biodegradable gradient layer system, involve growth factors. Growth factors useful in the present invention include, but are not limited to, transforming growth factor☐☐ ("TGF-☐"), transforming growth factor☐ β ("TGF-☐β"), platelet-derived growth factors including the AA, AB and BB isoforms ("PDGF"), fibroblast growth factors ("FGF"), including FGF acidic isoforms 1 and 2, FGF basic form 2, and FGF 4, 8, 9 and 10, nerve growth factors ("NGF") including NGF 2.5s, NGF 7.0s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), colony stimulating factors such as e.g. granulocyte colony stimulating factor (G-CSF) or granulocyte-macrophage colony stimulating factor (GMCSF), insulin like growth factor (IGF) I and II, hepatocyte growth factor, glial neurotrophic growth factor (GDNF), stem cell factor (SCF), keratinocyte growth factor (KGF), transforming growth factors (TGF), including TGFs alpha, beta, beta1, beta2, and beta3, skeletal growth factor, bone matrix derived growth factors, and bone derived growth factors and mixtures thereof. Some preferred growth factors include VEGF (vascular endothelial growth factor), NGFs (nerve growth factors), PDGF-AA, PDGF-BB, PDGF-AB, FGFb, FGFa, and BGF.

Cytokines, which may be likewise contained in the inventive biocompatible and preferably biodegradable gradient layer system; involve, but are not limited to, cardiotrophin, stromal cell derived factor, macrophage derived chemokine (MDC), melanoma growth stimulatory activity (MGSA), macrophage inflammatory proteins 1 alpha (MIP-1alpha), 2, 3 alpha, 3 beta, 4 and 5, IL-1, IL-2, IL-3, IL-4, IL-5, IL-6, IL-7, IL-8, IL-9, IL-10, IL-11, IL-12, IL-13, IL-15, IL-16, IL-17 and IL-18, TNF-α, and TNF-β. Immunoglobulins useful in the present invention include, but are not limited to, IgG, IgA, IgM, IgD, IgE, and mixtures thereof. Other molecules, which may be contained in the inventive biocompatible and preferably biodegradable gradient layer system; involve, but are not limited to, leptin, leukemia inhibitory factor (LIF), GLP-1, endostatin, angiostatin, thrombospondin, osteogenic protein-1, bone morphogenetic proteins 2 and 7, osteonectin, somatomedin-like peptide, osteocalcin, interferon alpha, interferon alpha A, interferon beta, interferon gamma, interferon 1 alpha.

The inventive biocompatible and preferably biodegradable gradient layer system may furthermore comprise an RGD peptide or sequence, preferably a repetitive RGD-binding peptide, more preferably having the formula $(RGD)_n$, for binding or adhering cells thereto. Typically, such a repetitive RGD-binding peptide of formula $(RGD)_n$ of the multifunctional fusion protein may be a peptide containing at least one RGD-peptide sequence, preferably at least two RGD-peptide sequences, or even three, four five or more RGD-peptide sequences, i.e. n may be 1, 2, 3, 4, 5 or even more, preferably, n is 1 to 5, 1 to 4, 1 to 3, 2 to 5, 2 to 4, 2 or 3 or 3 to 5, 3 to 4 or 4 to 5. In this context, a RGD peptide sequence is typically a sequence containing the three (consecutive) amino acids RGD, which is the one-letter amino acid code abbreviation for "Arginine-Glycine-Aspartate", in preferably the indicated order. Such a RGD sequence typically represents a part of the recognition sequence for integrins to extracellular matrix proteins. In this context, integrins are known as receptors that mediate attachment between a cell and the tissues surrounding it, e.g. other cells or the extracellular matrix (ECM). Integrins also play a role in cell signaling and thereby define cellular shape, mobility, and regulate the cell cycle. RGD-sequences, which may be utilized for the inventive purpose to allow binding of a cell to the multivalent fusion protein via integrins, are typically derived from an ECM protein or peptide comprising an RGD peptide sequence, or a synthetic sequence, in each case comprising the amino acid sequence Arginine-Glycine-Aspartate ("RGD" in the one-letter amino acid code). Such cell-specific adhesion sequences which might be incorporated in the inventive multifunctional fusion protein are e.g. as reviewed and listed by Hersel et al. (2003) (see Hersel et al., Biomaterials 24 (2003), 4385-4415). The respective disclosure in Hersel et al. (2003, supra) directed to such specific RGD peptide sequences and the specific RGD sequences as disclosed therein are preferably incorporated herein in their entirety by reference. Even more preferably, such RGD sequences may be selected, without being limited thereto, from at least one of the following amino acid sequences: RGD (SEQ ID NO: 1), RGDS (SEQ ID NO: 2), (RGDS)$_n$ (SEQ ID NO: 3), wherein n is preferably 1, 2, 3, 4, 5, 6, 7, 8, 9, 10 or even more, GRGD (SEQ ID NO: 4), RGDV (SEQ ID NO: 5), RGDT (SEQ ID NO: 6), GRGDG (SEQ ID NO: 7), GRGDS (SEQ ID NO: 8), GRGDY (SEQ ID NO: 9), GRGDF (SEQ ID NO: 10), YRGDS (SEQ ID NO: 11), YRGDG (SEQ ID NO: 12), YGRGD (SEQ ID NO: 13), GRGDSP (SEQ ID NO: 146), GRGDSG (SEQ ID NO: 15), GRGDSP (SEQ ID NO: 16), GRGDSY (SEQ ID NO: 17), GRGDVY (SEQ ID NO: 18), GRGDSPK (SEQ ID NO: 19), CGRGDSPK (SEQ ID NO: 20), CGRGDSY (SEQ ID NO: 21), YAVTGRGDS (SEQ ID NO: 22) (RGD mimetic tyrosine scaffold), AcCG-GNGEPRGD (SEQ ID NO: 23), YRAY-NH$_2$ (SEQ ID NO: 24), AcGCGYGRGDSPG (SEQ ID NO: 25), RGDS-PASSKP (SEQ ID NO: 26), AcGRGDSPASSKG (SEQ ID NO: 27),
or may be selected from cyclic RGD-sequences, such as βAXEPRGDNYRC (SEQ ID NO: 28), wherein X represents the modified amino acid Dap (2,3-diamino propionic acid), βA represents b-alanine and this cyclic RGD-sequence has the following structure:

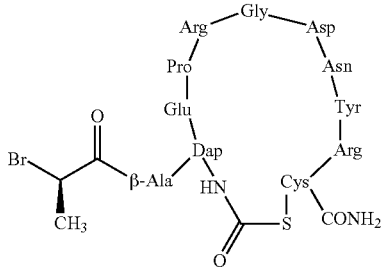

KRGDf (SEQ ID NO: 29), wherein f represents the D-amino acid variant of phenylalanine, and wherein this cyclic RGD-sequence has the following structure:

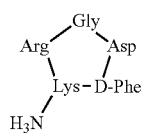

GPenGRGDSPCA (SEQ ID NO: 30), wherein Pen represents Penicillin, and wherein this cyclic RGD-sequence has the following structure:

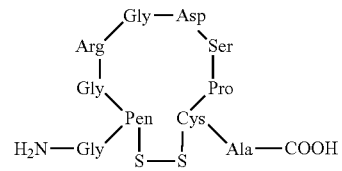

vRGDE (SEQ ID NO: 31), wherein v represents the D-amino acid variant of valine, and wherein this cyclic RGD-sequence has the following structure:

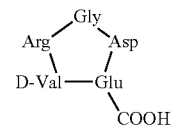

or may be selected from an amino acid sequence showing at least 80%, preferably at least 90%, more preferably at least 95%, and even more preferably at least 97.5% identity to the sequence of any of SEQ ID NO's 1 to 31.

One further additive, which may be contained in the inventive biocompatible and preferably biodegradable gradient layer system may, may be an anti-bacterial agent. In this context, any anti-bacterial agents known to one of skill in the art may be used. Non-limiting examples of anti-bacterial agents include Amikacin, Amoxicillin, Amoxicillin-clavulanic acid, Amphothericin-B, Ampicillin, Ampicllin-sulbactam, Apramycin, Azithromycin, Aztreonam, Bacitracin, Benzylpenicillin, Caspofungin, Cefaclor, Cefadroxil, Cefalexin, Cefalothin, Cefazolin, Cefdinir, Cefepime, Cefixime, Cefmenoxime, Cefoperazone, Cefoperazone-sulbactam, Cefotaxime, Cefoxitin, Cefbirome, Cefpodoxime, Cefpodoxime-clavulanic acid, Cefpodoxime-sulbactam, Cefbrozil, Cefquinome, Ceftazidime, Ceftibutin, Ceftiofur, Ceftobiprole, Ceftriaxon, Cefuroxime, Chloramphenicole, Florfenicole, Ciprofloxacin, Clarithromycin, Clinafloxacin, Clindamycin, Cloxacillin, Colistin, Cotrimoxazol (Trimthoprim/sulphamethoxazole), Dalbavancin, Dalfopristin/Quinopristin, Daptomycin, Dibekacin, Dicloxacillin, Doripenem, Doxycycline, Enrofloxacin, Ertapenem, Erythromycin, Flucloxacillin, Fluconazol, Flucytosin, Fosfomycin, Fusidic acid, Garenoxacin, Gatifloxacin, Gemifloxacin, Gentamicin, Imipenem, Itraconazole, Kanamycin, Ketoconazole, Levofloxacin, Lincomycin, Linezolid, Loracarbef, Mecillnam (amdinocillin), Meropenem, Metronidazole, Meziocillin, Mezlocillin-sulbactam, Minocycline, Moxifloxacin, Mupirocin, Nalidixic acid, Neomycin, Netilmicin, Nitrofurantoin, Norfloxacin, Ofloxacin, Oxacillin, Pefloxacin, Penicillin V, Piperacillin, Piperacillin-sulbactam, Piperacillin-tazobactam, Rifampicin, Roxythromycin, Sparfloxacin, Spectinomycin, Spiramycin, Streptomycin, Sulbactam, Sulfamethoxazole, Teicoplanin, Telavancin, Telithromycin, Temocillin, Tetracyklin, Ticarcillin, Ticarcillinclavulanic acid, Tigecycline, Tobramycin, Trimethoprim, Trovafloxacin, Tylosin, Vancomycin, Virginiamycin, and Voriconazole.

The inventive biocompatible and preferably biodegradable gradient layer system may be specifically shaped, for instance in the shape of a nerve guide, skin patch, fascial sheath, or a vascular graft for subsequent use in vivo. Likewise, the inventive biocompatible and preferably biodegradable gradient layer system may be shaped to fit a defect or site to be filled, preferably as a hard tissue or a soft tissue implant. Examples include a site from which a tumor has been removed, an injury site in the skin (a cut, a biopsy site, a hole or other defect) and a missing or shattered piece of bone. The inventive biocompatible and preferably biodegradable gradient layer system may be shaped into forms useful for substance delivery, for example, a skin or other epithelial patch, a lozenge for ingestion, an intraperitoneal implant, a subdermal implant, the interior or exterior lining of a stent, a cardiovascular valve, a tendon, a cornea, a ligament a dental prosthesis, a muscle implant, or a nerve guide. Preparation of the inventive biocompatible and preferably biodegradable gradient layer system allows great flexibility and allows for customizing the construct to virtually any shape needed. Many such gradient layer systems are sufficiently flexible to allow them to be formed to virtually any shape. In shaping such gradient layer systems, portions of the gradient layer system may be sealed to one another by, for example, heat sealing, chemical sealing, and application of mechanical pressure or a combination thereof. An example of heat sealing is the use of crosslinking techniques discussed herein to form crosslinking between two layers or sets of layers of the inventive biocompatible and preferably biodegradable gradient layer system may. Sealing may also be used to close an opening in a shaped matrix. Suturing may also be used to attach portions of matrices to one another or to close an opening in a matrix. It may be preferable that inclusion of synthetic polymers enhances the ability of the inventive biocompatible and preferably biodegradable gradient layer system to be heat sealed.

In this context, the geometry of the inventive biocompatible and preferably biodegradable gradient layer system can be modified to produce a desired matrix or form. By varying the ground geometry, for instance having a planar or linear or multiple points ground, the direction of the components of the inventive biocompatible and preferably biodegradable gradient layer system can be varied and customized to a particular application. For instance, a grounded target comprising a series of parallel lines can be used in preparing the inventive biocompatible and preferably biodegradable gradient layer system to orient electrospun materials in a specific direction. The grounded target can be a cylindrical mandrel whereby a tubular matrix is formed. Most preferably, the ground is a variable surface that can be controlled by a microprocessor that dictates a specific ground geometry that is programmed into it. Alternatively, for instance, the ground can be mounted on a frame that moves in the x, y, and z planes with respect to a fiber source or a stationary micropipette tip streaming collagen.

The inventive biocompatible and preferably biodegradable gradient layer system may be applied in a broad array of potential uses. Uses include, but are not limited to the following: manufacture of engineered tissue and organs, including structures such as patches, plugs or tissues or structures of matrix material. These and other constructs can be supplemented with cells or used without cellular supplementation. Additional uses include the following: prosthetics, and other implants; tissue scaffolding; repair or dressing of wounds; hemostatic devices; devices or structures for use in tissue repair and support such as sutures, adhesives, natural coatings or components for synthetic implants; cosmetic implants and supports; repair or structural support for organs or tissues; substance delivery; bioengineering platforms; platforms for testing the effect of substances upon cells; cell culture; and numerous other uses.

In each of the therapeutic uses outlined below, a therapeutically effective amount of the inventive biocompatible and preferably biodegradable gradient layer system is used. The therapeutically effective dosage amount of the inventive biocompatible and preferably biodegradable gradient layer system will vary somewhat from gradient layer system to gradient layer system, patient to patient, use to use, and will depend upon factors such as the condition of the patient, the nature of the condition being treated, and the route of delivery. For example, a small dermal defect 1 cm in diameter and 0.5 cm deep would require approximately 0.4 $cm^3$ of inventive biocompatible and preferably biodegradable gradient layer system to fill the void, stimulate vasculogenesis and tissue regeneration and have therapeutic efficacy. In contrast, a decubitus ulcer 20 cm in diameter and 5 cm deep would require approximately 1600 $cm^3$ of inventive biocompatible and preferably biodegradable gradient layer system to have similar efficacy. As a general proposition, the amount of inventive biocompatible and preferably biodegradable gradient layer system required for therapeutic efficacy may be from 0.1 to 2000 $cm^3$, preferably from about 0.5 to 100 $cm^3$.

In particular, the inventive biocompatible and preferably biodegradable gradient layer system can be used as biomaterials for regenerative medicine, particularly as a wound dressing or for tissue support or for preparation of same. Such an inventive biocompatible and preferably biodegradable gradient layer system may be also used for preparation of vascular constructs or a tissue or organ construct or as a corresponding construct, for substance delivery, e.g. localized delivery of therapeutic/biological agents, as well as controlled release of such agents at the target site in a subject, etc.

According to one aspect, the inventive biocompatible and preferably biodegradable gradient layer system can be used to construct blood vessels. One application of the inventive biocompatible and preferably biodegradable gradient layer system is in the formation of medium and small diameter vascular constructs. Some preferred materials for this aspect are gelatin, collagen and elastin, especially collagen type I and collagen type III. Examples of vascular constructs, which may be prepared according to the invention, include, but are not limited to coronary vessels for bypass or graft, femoral artery, popliteal artery, brachial artery, tibial artery, radial artery or corresponding veins. The inventive biocompatible and preferably biodegradable gradient layer system is useful especially when combined with endothelial cells and smooth muscle cells as well as pericytes. More complicated shapes including tapered and/or branched vessels can also be constructed. A different-shaped mandrel is necessary to wind the large fibers around or to orient the electrospun polymer.

Some of the complications with vascular matrices are (1) thrombus formation and (2) inability to quantitatively monitor integration of the vascular graft in vivo. Problems with thrombus formation are some of the most difficult challenges resulting in frequent failure of vascular grafts. Heparin, a powerful anticoagulation agent, is commonly administered clinically to avoid thrombus formation. However, systemic use of heparin carries a certain amount of risk, thus locally administered heparin is preferred. The inventive biocompatible and preferably biodegradable gradient layer system thus can be used to overcome the lack of control of drug release by incorporating heparin into the structure.

The inventive biocompatible and preferably biodegradable gradient layer system can likewise be used to construct engineered tissue or organ constructs, or parts of organ constructs e.g., heart, heart valves, liver, kidney, and the like. The ability to use inventive biocompatible and preferably biodegradable gradient layer system to bioengineer tissue or organs creates a wide variety of bioengineered tissue replacement applications. Examples of bioengineered components include, but are not limited to, blood vessels, heart, liver, kidney, skeletal muscle, skin and other epithelia, cardiac muscle, and nerve guides. In some aspects, such inventive biocompatible and preferably biodegradable gradient layer systems may be combined with therapeutic agents that improve the function of the implant. For example, antibiotics, anti-inflammatories, local anesthetics, growth factors and cytokines or combinations thereof, can be added to the inventive biocompatible and preferably biodegradable gradient layer system of a bioengineered organ to speed the healing process and reduce discomfort.

The inventive biocompatible and preferably biodegradable gradient layer system can also be used to deliver one or more therapeutic agents to a desired location.

The inventive biocompatible and preferably biodegradable gradient layer system may be used for e.g. treatments in the field of implantology, dermatology and of carcinomas in the oral cavity, in the upper aerodigestive tract (e.g. during otorhinolaryngology or ear nose throat medicine) as well as wounds of the oral cavity (e.g. during oral and maxillofacial surgery). More precisely, such clinical applications include e.g. wound dressings, tissue-supporting or tissue regenerating applications in the field of regenerative medicine, dental medicine and dentistry. Among such applications, for example chronically ulcerating wounds may be treated within the field of dermatology as well as wounds in the field of regenerative medicine, in particular wounds, which may occur during surgical excision of carcinomas of the upper aerodigestive tract (e.g. during otorhinolaryngology or ear nose throat medicine) as well as wounds of the oral cavity (e.g. during oral and maxillofacial surgery). In case of ulcerating wounds, which arise frequently in the lower part of the leg extremities with diabetes patients, autologous keratinocytes may be cultivated in vitro inventive on the inventive biocompatible and preferably biodegradable gradient layer system in the presence of irradiated cell division inactivated corresponding fibroblasts, until a preformed epithelium is obtained. Such autologous keratinocytes typically originate for example from the external hair root sheath, and are thus readily available. Subsequently, the inventive biocompatible and preferably biodegradable gradient layer system, which has been cultivated accordingly with such autologous cells, are preferably administered onto a preferably pretreated wound of the same patient the cells were derived from. Administration of the inventive biocompatible and preferably biodegradable gradient layer system onto the wound of the patient typically occurs in a density and size, which preferably initiates healing of the wound and preferably allows support of the cells with nutrients from the surrounding tissue and fluids. Administration of the inventive biocompatible and preferably biodegradable gradient layer system also support occlusion of the wound due to a directed and systematic degradation of the inventive biocompatible and preferably biodegradable gradient layer system and the resulting release of specific proteins, such as keratinocyte promoting growth factors, such as EGF or FGF-7 (KGF). With respect to carcinomas of the upper aerodigestive tract (e.g. during otorhinolaryngology or ear nose throat medicine) as mentioned herein, the keratinocytes applied with the inventive biocompatible and preferably biodegradable gradient layer system are typically derived from a so-called "forearm flap". In this case a piece of the entire skin of a part of the inner side of the forearm is removed and the fibroblasts of the connective tissue and the epithelial keratinocytes are grown in vitro. Since patients with such tumors typically suffer from impaired wound healing and accordingly show a correspondingly problematic granulation tissue, treatment of such patients and surgical dressing advantageously occurs under administration of the inventive biocompatible and preferably biodegradable gradient layer system, preferably seeded with epithelial cells and corresponding fibroblasts.

Further advantageous clinical applications of the inventive biocompatible and preferably biodegradable gradient layer system, preferably in form of a medicament, medical carrier, medical device or medical product, include alveolar crest prevention after tooth extraction in a patient to be treated. Such applications may decisively contribute to the aesthetically and functionally successful application of dental implants in the dental medicine and dentistry. In Germany over 14 million teeth are extracted each year. Subsequent to dental extraction or dental loss the supporting bone of the lost tooth more or less collapses to some extent (atrophy). Accordingly, different degrees of bone loss or atrophy can be observed in this context. With an atrophy of the alveolar bone the aesthetic appearance may be impaired. Even worse, the prerequisites for implantology and further prosthetic rehabilitation are impaired. Augmentative measures to improve the function and the aesthetic appearance are therefore usually necessary and thus usually increase financial expenses and the surgical workload with respect to invasive operation procedures. Accordingly, the specific application of the inventive biocompatible and preferably biodegradable gradient layer system directly subsequent to tooth extraction or loss represents an adequate and cost efficient tool to avoid such expenses and subsequent treatments.

Additional advantageous clinical applications of the inventive biocompatible and preferably biodegradable gradient layer system, preferably in form of a medicament, medical carrier, medical device or medical product, include the treatment of diseases of the human cornea in a patient to be treated. Such applications may be carried out in the treatment of diseases of the cornea, i.e. epithelium, connective tissue/fibroblasts, and endothelium. In diseases of the limbus ("limbus stem cell insufficiency") the vessel carrying cloudy epithelium of the connective tissue (conjunctiva) grows into the clear cornea typically resulting in blindness of the affected patient. Conventional treatment of such diseases typically requires a replacement of the limbus stem cells, which represent precursor cells of the clear cornea epithelium. In cases of one-sided diseases of the limbus the treatment may be carried out by transferring vital limbus tissue from the unaffected eye to the affected eye. In cases of an ambilateral such a treatment is not possible and much more problematic. In these cases, provided there is a remaining limbal function at least in one eye, a confluent cell layer may be grown on a suitable carrier matrix such as the inventive biocompatible and preferably biodegradable gradient layer system based on a small cell sample. The confluent cell layer may then be transferred to the affected eye. Until today a human amnion membrane or a fibrin gel was used as a carrier matrix, wherein the number of proliferating cells (stem cells) grown from the extracted cell sample represented the most critical aspect of such an ex vivo culture. Unfortunately, long term observations revealed poor number of stem cells on both of the carrier matrices presently used, i.e. the human amnion membrane or the fibrin gel. The reason for this failure is most likely the fact that none of these carrier matrices provide the optimal extracellular environment for such stem cells. Accordingly, these stem cells can not form a niche required for an optimal cell growth. In this context, the inventive biocompatible and preferably biodegradable gradient layer system provides an optimal environment due to their individually adaptable properties, which can be designed with respect to the requirement of these stem cells.

Another clinical application of the inventive biocompatible and preferably biodegradable gradient layer system, preferably in form of a medical device, includes the treatment of large chronic wounds, wounds caused by a disease, such as e.g. cancer, diabetes, etc., e.g. as a volume replacement, etc., in particularly the treatment of lesions and loss of tissue and tissue structures, e.g. in the field of dermatology. In this context, the inventive biocompatible and preferably biodegradable gradient layer system provides a superior candidate for the preparation of dermal equivalents, or, in combination with fibroblasts, may be used advantageously as a carrier system or scaffold structure for epithelial keratinocytes, all of which are included herein. Applications, may comprise the treatment of wounds of (i) patients with ulcerating wounds, e.g. at the extremities due to diabetes type II, or (ii) after tumor dissections. The inventive biocompatible and preferably biodegradable gradient layer system effectively stimulates healing of the wound and thus accelerates the healing process after transplantation.

Further clinical applications of the inventive biocompatible and preferably biodegradable gradient layer system, preferably in form of a medical device, include the treatment of diseases of the endothelium of the cornea. A specific application in this context is e.g. treatment of Fuchs' endothelial dystrophy of the cornea. In this disease but also in the context of other diseases, a drastic reduction of the cells of the corneal endothelium occurs due to apoptosis leading to a cloudy cornea. The present therapy includes transplantation of the cornea including transplantation or replacement of all layers of the cornea. An alternative treatment includes replacement of diseased cells by a specific transplantation of the endothelial layer from a donor. Since the transplantation material is no HLA identical material the tissue graft may be rejected resulting in a significant damage of the endothelial layer. In this context, the inventive biocompatible and preferably biodegradable gradient layer system provide the possibility to extract endothelial cells from the patient to be treated and to enrich these endothelial cells similar to the above by growing a confluent cell layer on a suitable carrier matrix such as the inventive biocompatible and preferably biodegradable gradient layer system based on a small cell sample. Again, the inventive biocompatible and preferably biodegradable gradient layer system provides an optimal environment for these cells due to their individually adaptable properties, which can be designed with respect to the requirement of these stem cells. The cells may then be transferred together with inventive biocompatible and preferably biodegradable gradient layer system as a carrier to the backside of the cornea and thus to avoid rejection of the graft.

The inventive biocompatible and preferably biodegradable gradient layer system, preferably in form of a medicament, medical carrier, medical device or medical product, may furthermore be used, e.g. in burn dressings, hemeostatic patches, in the treatment of lesions, in the surgical dressing, for wound treating, for soft or hard tissue regeneration, e.g. in the field of implantology, for the treatment of wounds in the oral cavity, e.g. due to tumor diseases, in the field of ophthalmology, in the field of periodontal defects, including periodontal ligament etc., for preparing a cell implant for, integrally or partially, regenerating or reconstructing damaged or ill or removed tissues, in particular muscle, myocardium, connective, bone, tendon or ligamentous, hepatic, renal, corneal, dermis or epidermis and other epithelial tissue, articular cartilagenous tissue, for preparing an implant of central nervous system cells as neuronal cells for, integrally or partially, regenerating or reconstructing neuronal tissue, in particular central nervous system tissue, nervous tissue, such as neuronal tissue, damaged as a result of Parkinson's disease or spinal marrow damages or oncologic pathologies or Alzheimer's disease, nervous tissue, such as neuronal tissue, removed or ablated, following an surgical operation. The inventive biocompatible and preferably biodegradable gradient layer system may furthermore be used in the treatment of cardiovascular diseases, treatment of traumatologic diseases or lesions, treatment of diseases or disorders in the field of orthopedic, treatment, regeneration or reconstitution of cartilage, cartilage diseases or cartilage disorders, chondropahty, constitution of cartilage in the knee, and the treatment of joint diseases or as a drug delivery device, cell matrices for in vitro, in vivo and/or ex vivo applications, or for preparation of tissue models and as cell transplantation matrices.

Accordingly, the object underlying the present invention is furthermore solved by a biomaterial, comprising a gradient layer system as defined herein, wherein the biomaterial is selected from a biomaterial for regenerative medicine for wound dressings or for tissue support or for preparation of same, a bioengineered tissue or organ constructs, or a part of organ constructs, a bioengineered heart, a bioengineered heart valve, a bioengineered liver, a bioengineered kidney, a bioengineered blood vessel, a bioengineered skeletal muscle, a bioengineered cardiac muscle, a bioengineered nerve guide, a burn dressing, a wound dressing, a surgical dressing, a skin patch, an oral patch or any other epithelial patch, a fascial sheath, a vascular construct, a vascular graft, a blood vessel, a coronary vessel for bypass or graft, a femoral artery, a popliteal artery, a brachial artery, a tibial artery, a radial artery or corresponding vein, a stent, the interior or exterior lining of a stent, a cardiovascular valve, a skin patch, a lozenge for ingestion, an intraperitoneal implant, a subdermal implant, a tendon, a cornea, a ligament, a dental prosthesis, a muscle implant, or a nerve guide, an engineered tissue or organ, prosthetics, a tissue scaffold, a hemostatic device, a device or structures for tissue repair and support adhesives, a natural coating or component for synthetic implants; a cosmetic implant or support, a biomaterial for substance delivery, a bioengineering platforms, or a platform for testing the effect of substances upon cells.

According to another specific embodiment, the object underlying the present invention is furthermore solved by the use of the inventive biocompatible and preferably biodegradable gradient layer system in the treatment of diseases, disease states or treatments in general as defined herein as mentioned above. More preferably, the inventive biocompatible and preferably biodegradable gradient layer system as defined herein may be used (e.g. in the preparation of a medicament, a medical carrier, a medical device or a medical product) for the treatment of diseases as defined above.

The inventive biocompatible and preferably biodegradable gradient layer system can be stored and used shortly before implantation by seeding it with cells. The inventive biocompatible and preferably biodegradable gradient layer system may be dry once it is prepared and can be stored in a dry or frozen state. Storage conditions will depend on the inventive biocompatible and preferably biodegradable gradient layer system used and whether a therapeutic agent is incorporated onto or into the gradient layer system. In aspects where a therapeutic agent is incorporated, the inventive biocompatible and preferably biodegradable gradient layer system can be stored at temperatures below 0° C., under vacuum, or in a lyophilized state. Other storage conditions can be used, for example, at room temperature, in darkness, in vacuum or under reduced pressure, under inert atmospheres, at refrigerator temperature, in aqueous or other liquid solutions, or in powdered form depending on the materials in and on the inventive biocompatible and preferably biodegradable gradient layer system.

The inventive biocompatible and preferably biodegradable gradient layer system may also be sterilized through conventional means known to one of ordinary skill in the art such as radiation, and heat. The inventive biocompatible and preferably biodegradable gradient layer system can also be combined with bacteriostatic agents, such as thimerosal, to inhibit bacterial growth. In some aspects, the compositions can be treated with chemicals, solutions, or processes that confer stability in storage and transport.

The inventive biocompatible and preferably biodegradable gradient layer system may be provided as such or in form of a medicament, medical carrier, medical device or medical product for any of the above defined uses.

In the present invention, if not otherwise indicated, different features of alternatives, aspects and embodiments may be combined with each other, if suitable. Furthermore, the term "comprising" shall not be construed as meaning "consisting of", if not specifically mentioned. However, in the context of the present invention, term "comprising" may be substituted with the term "consisting of", where applicable.

FIGURES

The figures shown in the following are merely illustrative and shall describe the present invention in a further way. These figures shall not be construed to limit the present invention thereto.

FIG. 1: illustrates an exemplary inventive biocompatible and preferably biodegradable gradient layer system and its structure. As can be seen, the inventive gradient layer system comprises different sets of layers comprising a biocompatible and preferably biodegradable cross-linked polymer present in a fleece like structure and at least one biocompatible and preferably biodegradable support layer present in a net or mesh-like structure.

Figure 2:
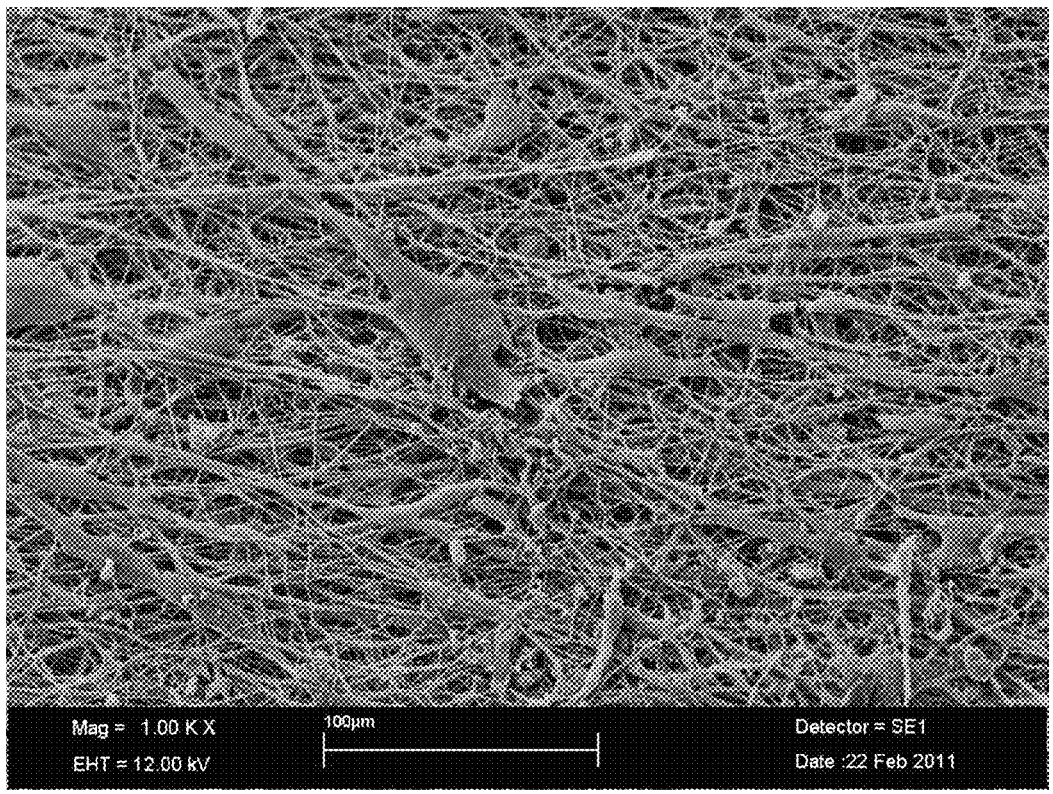

FIG. 2: shows a raster electron microscopy (REM) of an inventive biocompatible and preferably biodegradable gradient layer system, wherein fibroblasts of the dermis were cultivated and propagated successfully in vitro. The raster electron microscopy (REM) pictures in FIG. 2 additionally show the pre-culture of fibroblasts from the dermis on the bottom side/undersurface (inlay) of the inventive gradient layer system and establishment of an epidermal keratinocytes compartment on the surface of the substrate.

Figure 3:
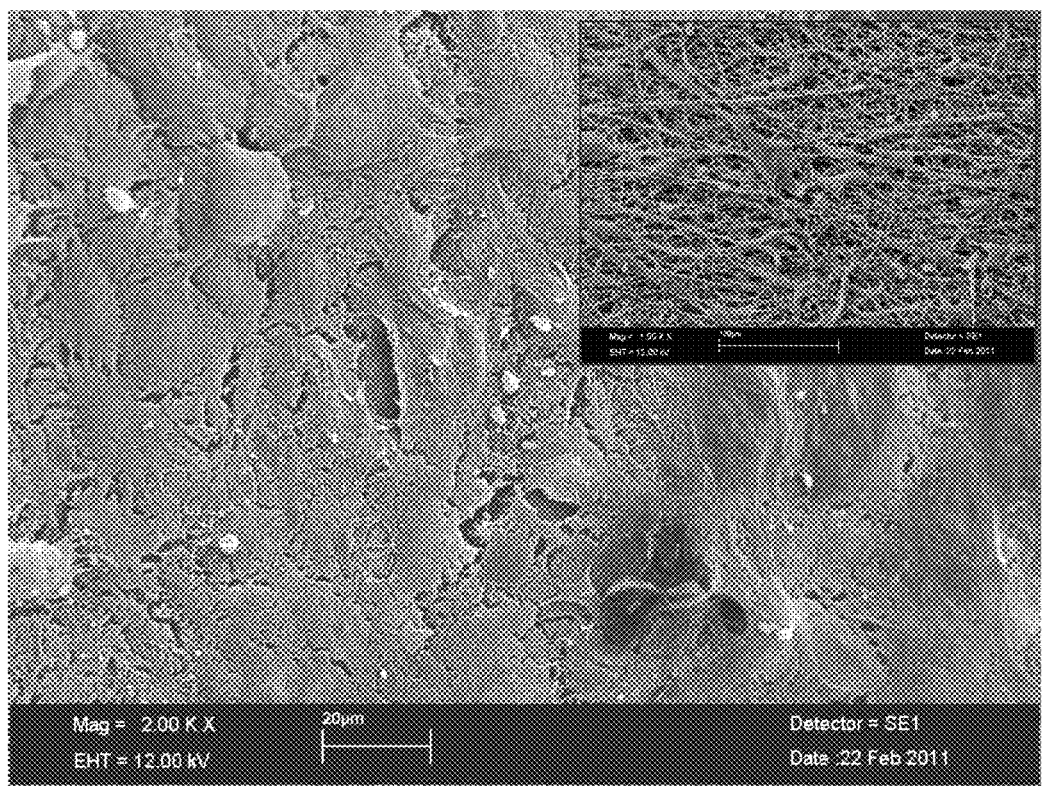

FIG. 3: depicts a raster electron microscopy (REM) of an inventive gradient layer system, wherein an interactive co-culture of fibroblasts of the dermis and epithelial keratinocytes were cultivated and propagated successfully in vitro on the inventive gradient layer system (see FIG. 3 and inlay).

EXAMPLES

The examples shown in the following are merely illustrative and shall describe the present invention in a further way. These examples shall not be construed to limit the present invention thereto.

Example 1—Preparation of Gelatin Layers

Gelatin (type B from bovine skin; Sigma-Aldrich) was solubilized in a solvent mixture of acetic acid (Merck), ethyl acetate (Fluka) and water (5:3:2 vol). The concentration was in a range of about 5 and 20% (weight). Different amounts of cross-linker glyoxal (0.0005-0.1 g/g gelatin solution) were mixed with the gelatin solution. The gelatine/glyoxal mixture was filled into a syringe and mounted in a syringe pump (Model: KDS100 oder KDS101, KD scientific). the flow rate was between about 0.1 und 1.0 ml/h. Between the cannula and the collector an electrical field was established with two high voltage power generators (Heinzinger® LNC 30000-2 neg und LNC 30000-2 pos) with field forces between 0.4 und 8 kV/cm.

a) Electrospin/Elektrospray

After depositing a sufficient thick fleece like set of layers of gelatin/glyoxal fibers on the substrate a thin layer of PCL was electrospun or electrosprayed on the fleece like set of layers formed by gelatin/glyoxal fibers. Subsequently further sets of layers comprising gelatin were applied. During the subsequent temperature treatment (60-100° C.; 0.5-24 h) a (further) cross-linking of the gelatin with glyoxal occurred. This was accompanied by a browning of the fleece like sets of layers due to formation to Schiff bases. Furthermore, temperature treatment led to a (partial) melting of the PCL layer. The melt punctually or laminarly surrounds the gelatin fibers and thus provides for significantly improved mechanical properties of the swollen fleece like set of layers of gelatin/glyoxal fibers.

b) 3D-Plotting

A plotted PCL layer construct was applied on the fleece like set of layers of gelatin/glyoxal fibers instead of the PCL layers as described under section a).

For both a) and b) it is to be noted that the arrangement of layers or sets of layers may be varied arbitrarily. As an example, it is likewise possible to use a 3D construct as a target for electrospinning. A different arrangement of the layers or sets of layers, the orientation of the different layers or sets of layers and a different number of layers or sets of layers is possible. Optionally, constructs, such as the PCL layers, etc., may be applied onto a support or directly onto the fleece like set of layers of gelatin/glyoxal fibers using a heat gun or hot air blower. A further possibility for improving the mechanical properties of the inventive biocompatible and preferably biodegradable gradient layer system was used based on an additional cross-linking of the gelatin fibers with polyphenol compounds, preferably gallotannine (Sigma-Aldrich). The fleece like set of layers of gelatin/glyoxal fibers was immersed or incubated in an aqueous or alcoholic solution (0.01-10% (weight)) of polyphenol compounds and agitated slightly between 0.5 and 24 h at temperatures of about 20-40° C. Excess polyphenol compounds were removed via several washing steps (destilled water, buffer, alcohol).

Example 2—Preparation of Polycaprolactone Layers

Abbreviations:
PCL=polycaprolactone
TCP=tricalciumphosphate
$D_{inside}$=bore diameter of nozzle
RPM=rounds per minute
Experimental Part of 3D-Bioplotting™
1. Polycaprolactone—Mesh Like Constructs The mesh like constructs were printed directly with a 3D-plotter (3$^{rd}$ Generation, Envisiontec, Germany) using CAD data. For this purpose polycaprolactone (PCL, $M_n$=80.000 g/mol, Aldrich, St. Louis, USA) was filled into the high temperature printer head of the 3D-Bioplotter and molten (90° C.). The molten material was printed in form of rectangles (4×4 cm). A teflon foil serves as a support for printing. All experimental parameters are listed in table 1.

TABLE 1

Experimental parameters of the plotting process for mesh-like constructs made from pure PCL.

| Material | Plotting medium | $T_{(material)}$ (° C.) | $T_{(plotting\ medium)}$ (° C.) | Nozzle | Nozzle $D_{inside}$ (mm) |
|---|---|---|---|---|---|
| PCL ($M_n$ = 80.000 g/mol) | Air | 90 | 20 | Stahl | 0.45 |

| Material | applied pressure (×10$^5$ Pa) | operating speed of printer head (mm/s) | distance of strands (mm) | thickness of layer (mm) | corner delay (s) |
|---|---|---|---|---|---|
| PCL ($M_n$ = 80.000 g/mol) | 3.6-3.8 | 100 | 4.5 | 0.3 | 0.1 |

2. Polycaprolactone/Tricalciumphosphate—Mesh-Like Constructs:

Polycaprolactone (PCL, $M_n$=80.000 g/mol, Aldrich, St. Louis, USA) and Tricalciumphosphate (10 Gew.-%, Budenheim, Germany) were provided in a lever lid glass container and mixed. The mixture was compounded with a microcompounder (Daca Instruments, Santa Barbara, USA) (100° C., 100 RPM, retention time 2 min). The obtained material was processed as indicated under section a. above. All experimental parameters are listed in table 2.

TABLE 2

Experimental parameter of the plotting process for mesh-like constructs made from PCL and TCP.

| Material | Plotting medium | $T_{(material)}$ (° C.) | $T_{(plotting\ medium)}$ (° C.) | Nozzle | Nozzle $D_{inside}$ (mm) |
|---|---|---|---|---|---|
| PCL/TCP ($M_n$ = 80.000 g/mol) | Luft | 90 | 20 | Stahl | 0.45 |

| Material | applied pressure (×10$^5$ Pa) | operating speed of printer head (mm/s) | distance of strands (mm) | thickness of layer (mm) | corner delay (s) |
|---|---|---|---|---|---|
| PCL/TCP ($M_n$ = 80.000 g/mol) | 3.5 | 100 | 4.5 | 0.3 | 0.1 |

Example 3—Preparation of a Biocompatible and Preferably Biodegradable Gradient Layer System For the preparation of an exemplary inventive gradient layer system gelatin or gelatin blends with other polymers as described above were prepared prior to synthesis of polymeric gelatin fibers and mixed with glyoxal as a crosslinker. In a first step of the inventive method polymeric gelatin fibers was then synthesized via an electrospin procedure as described before leading to a layer of cross-linked polymeric gelatin fibers. The fibers were synthesized using the gelatin blends in the presence of the cross-linker glyoxal to enhance mechanical properties. Furthermore, the fiber strength of the polymeric gelatin fibers was adjusted during the electrospin procedure due to increasing viscosity upon cross-linking the polypeptide with glyoxal. Glyoxal preferably renders the obtained vlies structure water insoluble and thus improves the mechanical properties of the biocompatible and preferably biodegradable gradient layer system. The increasing viscosity led to increasing fiber strength and resulted in a gradient in the layer produced with polymeric gelatin fibers. The gradual fiber strengths had a range as defined above, typically in a range of about 50 to 1500 nm or 100 to 800 nm.

Subsequently after synthesis of a layer of cross-linked polymeric gelatin fibers according to the first step those gradual fiber layers of polymeric gelatin fibers were identified, which exhibit a sufficient stability in aqueous milieu. The pH values were about 5.5 to about 8.5. Excessive alkaline and excessive acidic conditions were avoided to prevent degradation of the gelatin. These gradual fiber layers were then used as a basis in a second step in a 3D-electroplotting procedure. In the 3D-electroplotting procedure the polyester compound polycaprolactone was plotted onto the gradual fiber layer of polymeric gelatin fibers to obtain the inventive polymeric gradient layer system as a three-dimensional biohybrid polymer network structure or scaffold, which significantly stabilized the gradual fiber layer of polymeric gelatin fibers. The resultant scaffold retained the superior properties of the polymers used in the single steps. An exemplary biocompatible and preferably biodegradable gradient layer system and its structure are shown in FIG. 1.

The biocompatible and preferably biodegradable gradient layer system obtained according to step 2, as described before, was then cultured with target cells in a further step 3. Step 3 was carried out by cultivating target cells, preferably fibroblasts of the dermis, on the surface of the inventive polymeric gradient layer system. The target cells were cultivated in cell culture medium. Cultures of primary dermal fibroblasts were maintained for routine cell culture in DME medium (PAA, Pasching, Austria) containing 10% foetal calf serum (Seromed, Biochrom, Berlin, Germany) and 50 µg/ml kanamycin (Roche Diagnostics, Mannheim, Germany). Epidermal keratinocytes were maintained in low calcium keratinocyte growth medium (basal keratinocyte medium, KGM, with provided supplements, Promocell, Heidelberg, Germany), containing 50 µg/ml kanamycin (Roche Diagnostics, Mannheim, Germany).

Establishment of the respective cell types on the biocompatible and preferably biodegradable gradient layer system was performed by a 24 hours pre-cultivation of dermal fibroblasts at the bottom side of the substrate and subsequently by seeding epidermal keratinocytes at the top side of the device. This co-culture system has been cultivated for further 14 days.

As determined by raster electron microscopy (REM) (see FIG. 2) fibroblasts of the dermis were cultivated and propagated in vitro successfully. The raster electron microscopy (REM) pictures in FIG. 2 additionally show the pre-culture of fibroblasts from the dermis on the bottom side/undersurface (inlay) of the inventive polymeric gradient layer system and establishment of an epidermal keratinocytes compartment on the surface of the substrate. It was furthermore possible to successfully cultivate interactive co-cultures consisting of fibroblasts and epithelial keratinocytes on the inventive polymeric gradient layer system (see FIG. 3 and inlay).

The invention claimed is:

1. A biocompatible gradient layer system comprising:
   at least one biocompatible meltable support layer comprising polycaprolactone (PCL);
   at least one set of layers disposed on the at least one biocompatible meltable support layer; and
   a continuous fiber diameter gradient within the at least one set of layers,
      wherein the at least one set of layers comprises fibers of a biocompatible and biodegradable polymer,
   wherein the fibers of the biocompatible and biodegradable polymer are formed by electrospinning a solution containing crosslinkers and the biocompatible and biodegradable polymer,
   wherein the fibers of the biocompatible and biodegradable polymer are selected from gelatin or collagen,
   wherein the crosslinkers are selected from glyoxal or glyoxal-trimer-dihydrate,
   wherein the fibers of the biocompatible and biodegradable polymer are internally crosslinked with the crosslinkers glyoxal or glyoxal-trimer-dihydrate,
   wherein the fibers of the resulting biocompatible and biodegradable crosslinked polymer are loosely packed and not interconnected to each other,
   wherein the continuous fiber diameter gradient is formed by crosslinking during the electrospinning process,
   wherein the diameter of the polymeric fibers is increased within the at least one set of layers due to the continuous crosslinking, and
   wherein the polymeric fibers of the at least one set of layers have a diameter between about 1 nm to about 50 µm.

2. The gradient layer system according to claim 1, wherein the fiber diameter increases or decreases from about 0.0001 µm to about 1 µm per micrometer height of the set of layers either within the at least one set of layers or between several sets of layers of the gradient layer system.

3. The gradient layer system according to claim 1, wherein the at least one biocompatible support layer comprises
   an incorporable material selected from the group consisting of an incorporable ceramic material, an incorporable ceramic material made from tricalcium phosphate (TCP) and an incorporable ceramic material made from hydroxyl apatite (HA).

4. The gradient layer system according to claim 1, wherein the at least one set of layers comprising the biocompatible and biodegradable cross-linked polymer is present in the form of a fleece, a net or a mesh-like structure.

5. The gradient layer system according to claim 1, wherein the at least one biocompatible support layer is present in the form of bands, strands, fibers, particles, drops, a net or mesh-like structures, a sheet, a film, a foil, or a laminate.

6. The gradient layer system according to claim 1, wherein the gradient layer system is seeded with cells.

7. The gradient layer system according to claim 6, wherein the cells are selected from mammalian, human or non-human cells selected from committed stem cells, differentiated cells, adult stem cells, bone marrow stem cells, umbilical cord stem cells, engineered or non-engineered stem cells, primary or immortalized (cell-line) stem cells, and mesenchymal stem cells, or the cells are selected from a mixture of cells as defined before.

8. The gradient layer system according to claim 1, wherein the gradient layer system further comprises agents selected from cytokines, interleukins, growth factors, immunoglobulins, RGD-peptides, and antibacterial agents.

9. The gradient layer system according to claim 6, wherein the cells are selected from cartilage cells, epithelial cells, endothelial cells, endothelial cells of vascular tissue, endothelial cells of corneal tissue, skin cells, osteocytes, osteoblasts, cementoblasts, bone cells, myoblasts, neuroblasts, fibroblasts cells of all connective tissues including fibroblasts selected from gingival, skin or corneal fibroblasts, and fibroblasts selected from gingival, skin or corneal fibroblasts together with periodontal ligament fibroblasts, keratinocytes, gingival keratinocytes, glioblasts, germ cells, hepatocytes, chondrocytes, cardiac muscle cells, connective tissue cells, glial cells, hormone-secreting cells, cells of the immune system, neurons, cells of the central nervous system, neuronal cells, pericytes, myocytes, adipocytes, astrocytes, melanocytes, tissue cells, tissue cells from autologous tissue sources, tissue cells from allogenic tissue sources, tissue cells from xenogenic tissue sources, autologous cells, allogenic cells, xenogenic cells, tenocytes, cardiomyocytes, hepatocytes, and smooth muscle cells, or the cells are selected from a mixture of cells as defined before.

* * * * *

SEQUENCE LISTING

```
<160> NUMBER OF SEQ ID NOS: 31

<210> SEQ ID NO 1

<400> SEQUENCE: 1

000

<210> SEQ ID NO 2
<211> LENGTH: 4
<212> TYPE: PRT
<213> ORGANISM: Artificial Sequence
<220> FEATURE:
<223> OTHER INFORMATION: RGD peptide sequence

<400> SEQUENCE: 2

Arg Gly Asp Ser
1

<210> SEQ ID NO 3
<211> LENGTH: 4
<212> TYPE: PRT
<213> ORGANISM: Artificial Sequence
<220> FEATURE:
<223> OTHER INFORMATION: RGD peptide sequence
<220> FEATURE:
<221> NAME/KEY: REPEAT
<222> LOCATION: (1)..(4)
<223> OTHER INFORMATION: repeat number = 1-10

<400> SEQUENCE: 3

Arg Gly Asp Ser
1

<210> SEQ ID NO 4
<211> LENGTH: 4
<212> TYPE: PRT
<213> ORGANISM: Artificial Sequence
<220> FEATURE:
<223> OTHER INFORMATION: RGD peptide sequence
```

```
<400> SEQUENCE: 4

Gly Arg Gly Asp
1

<210> SEQ ID NO 5
<211> LENGTH: 4
<212> TYPE: PRT
<213> ORGANISM: Artificial Sequence
<220> FEATURE:
<223> OTHER INFORMATION: RGD peptide sequence

<400> SEQUENCE: 5

Arg Gly Asp Val
1

<210> SEQ ID NO 6
<211> LENGTH: 4
<212> TYPE: PRT
<213> ORGANISM: Artificial Sequence
<220> FEATURE:
<223> OTHER INFORMATION: RGD peptide sequence

<400> SEQUENCE: 6

Arg Gly Asp Thr
1

<210> SEQ ID NO 7
<211> LENGTH: 5
<212> TYPE: PRT
<213> ORGANISM: Artificial Sequence
<220> FEATURE:
<223> OTHER INFORMATION: RGD peptide sequence

<400> SEQUENCE: 7

Gly Arg Gly Asp Gly
1               5

<210> SEQ ID NO 8
<211> LENGTH: 5
<212> TYPE: PRT
<213> ORGANISM: Artificial Sequence
<220> FEATURE:
<223> OTHER INFORMATION: RGD peptide sequence

<400> SEQUENCE: 8

Gly Arg Gly Asp Ser
1               5

<210> SEQ ID NO 9
<211> LENGTH: 5
<212> TYPE: PRT
<213> ORGANISM: Artificial Sequence
<220> FEATURE:
<223> OTHER INFORMATION: RGD peptide sequence

<400> SEQUENCE: 9

Gly Arg Gly Asp Tyr
1               5

<210> SEQ ID NO 10
<211> LENGTH: 5
<212> TYPE: PRT
<213> ORGANISM: Artificial Sequence
<220> FEATURE:
<223> OTHER INFORMATION: RGD peptide sequence
```

```
<400> SEQUENCE: 10

Gly Arg Gly Asp Phe
1               5

<210> SEQ ID NO 11
<211> LENGTH: 5
<212> TYPE: PRT
<213> ORGANISM: Artificial Sequence
<220> FEATURE:
<223> OTHER INFORMATION: RGD peptide sequence

<400> SEQUENCE: 11

Tyr Arg Gly Asp Ser
1               5

<210> SEQ ID NO 12
<211> LENGTH: 5
<212> TYPE: PRT
<213> ORGANISM: Artificial Sequence
<220> FEATURE:
<223> OTHER INFORMATION: RGD peptide sequence

<400> SEQUENCE: 12

Tyr Arg Gly Asp Gly
1               5

<210> SEQ ID NO 13
<211> LENGTH: 5
<212> TYPE: PRT
<213> ORGANISM: Artificial Sequence
<220> FEATURE:
<223> OTHER INFORMATION: RGD peptide sequence

<400> SEQUENCE: 13

Tyr Gly Arg Gly Asp
1               5

<210> SEQ ID NO 14
<211> LENGTH: 6
<212> TYPE: PRT
<213> ORGANISM: Artificial Sequence
<220> FEATURE:
<223> OTHER INFORMATION: RGD peptide sequence

<400> SEQUENCE: 14

Gly Arg Gly Asp Ser Pro
1               5

<210> SEQ ID NO 15
<211> LENGTH: 6
<212> TYPE: PRT
<213> ORGANISM: Artificial Sequence
<220> FEATURE:
<223> OTHER INFORMATION: RGD peptide sequence

<400> SEQUENCE: 15

Gly Arg Gly Asp Ser Gly
1               5

<210> SEQ ID NO 16
<211> LENGTH: 6
<212> TYPE: PRT
<213> ORGANISM: Artificial Sequence
<220> FEATURE:
<223> OTHER INFORMATION: RGD peptide sequence
```

```
<400> SEQUENCE: 16

Gly Arg Gly Asp Ser Pro
1               5

<210> SEQ ID NO 17
<211> LENGTH: 6
<212> TYPE: PRT
<213> ORGANISM: Artificial Sequence
<220> FEATURE:
<223> OTHER INFORMATION: RGD peptide sequence

<400> SEQUENCE: 17

Gly Arg Gly Asp Ser Tyr
1               5

<210> SEQ ID NO 18
<211> LENGTH: 6
<212> TYPE: PRT
<213> ORGANISM: Artificial Sequence
<220> FEATURE:
<223> OTHER INFORMATION: RGD peptide sequence

<400> SEQUENCE: 18

Gly Arg Gly Asp Val Tyr
1               5

<210> SEQ ID NO 19
<211> LENGTH: 7
<212> TYPE: PRT
<213> ORGANISM: Artificial Sequence
<220> FEATURE:
<223> OTHER INFORMATION: RGD peptide sequence

<400> SEQUENCE: 19

Gly Arg Gly Asp Ser Pro Lys
1               5

<210> SEQ ID NO 20
<211> LENGTH: 8
<212> TYPE: PRT
<213> ORGANISM: Artificial Sequence
<220> FEATURE:
<223> OTHER INFORMATION: RGD peptide sequence

<400> SEQUENCE: 20

Cys Gly Arg Gly Asp Ser Pro Lys
1               5

<210> SEQ ID NO 21
<211> LENGTH: 7
<212> TYPE: PRT
<213> ORGANISM: Artificial Sequence
<220> FEATURE:
<223> OTHER INFORMATION: RGD peptide sequence

<400> SEQUENCE: 21

Cys Gly Arg Gly Asp Ser Tyr
1               5

<210> SEQ ID NO 22
<211> LENGTH: 9
<212> TYPE: PRT
<213> ORGANISM: Artificial Sequence
<220> FEATURE:
<223> OTHER INFORMATION: RGD peptide sequence
```

```
<400> SEQUENCE: 22

Tyr Ala Val Thr Gly Arg Gly Asp Ser
1               5

<210> SEQ ID NO 23
<211> LENGTH: 10
<212> TYPE: PRT
<213> ORGANISM: Artificial Sequence
<220> FEATURE:
<223> OTHER INFORMATION: RGD peptide sequence
<220> FEATURE:
<221> NAME/KEY: MOD_RES
<222> LOCATION: (1)..(1)
<223> OTHER INFORMATION: ACETYLATION

<400> SEQUENCE: 23

Cys Gly Gly Asn Gly Glu Pro Arg Gly Asp
1               5                   10

<210> SEQ ID NO 24
<211> LENGTH: 4
<212> TYPE: PRT
<213> ORGANISM: Artificial Sequence
<220> FEATURE:
<223> OTHER INFORMATION: RGD peptide sequence

<400> SEQUENCE: 24

Tyr Arg Ala Tyr
1

<210> SEQ ID NO 25
<211> LENGTH: 11
<212> TYPE: PRT
<213> ORGANISM: Artificial Sequence
<220> FEATURE:
<223> OTHER INFORMATION: RGD peptide sequence
<220> FEATURE:
<221> NAME/KEY: MOD_RES
<222> LOCATION: (1)..(1)
<223> OTHER INFORMATION: ACETYLATION

<400> SEQUENCE: 25

Gly Cys Gly Tyr Gly Arg Gly Asp Ser Pro Gly
1               5                   10

<210> SEQ ID NO 26
<211> LENGTH: 10
<212> TYPE: PRT
<213> ORGANISM: Artificial Sequence
<220> FEATURE:
<223> OTHER INFORMATION: RGD peptide sequence

<400> SEQUENCE: 26

Arg Gly Asp Ser Pro Ala Ser Ser Lys Pro
1               5                   10

<210> SEQ ID NO 27
<211> LENGTH: 11
<212> TYPE: PRT
<213> ORGANISM: Artificial Sequence
<220> FEATURE:
<223> OTHER INFORMATION: RGD peptide sequence
<220> FEATURE:
<221> NAME/KEY: MOD_RES
<222> LOCATION: (1)..(1)
<223> OTHER INFORMATION: ACETYLATION
```

```
<400> SEQUENCE: 27

Gly Arg Gly Asp Ser Pro Ala Ser Ser Lys Gly
1               5                   10

<210> SEQ ID NO 28
<211> LENGTH: 11
<212> TYPE: PRT
<213> ORGANISM: Artificial Sequence
<220> FEATURE:
<223> OTHER INFORMATION: RGD peptide sequence
<220> FEATURE:
<221> NAME/KEY: MOD_RES
<222> LOCATION: (1)..(1)
<223> OTHER INFORMATION: bAla
<220> FEATURE:
<221> NAME/KEY: MOD_RES
<222> LOCATION: (2)..(2)
<223> OTHER INFORMATION: Dpr

<400> SEQUENCE: 28

Ala Xaa Glu Pro Arg Gly Asp Asn Tyr Arg Cys
1               5                   10

<210> SEQ ID NO 29
<211> LENGTH: 5
<212> TYPE: PRT
<213> ORGANISM: Artificial Sequence
<220> FEATURE:
<223> OTHER INFORMATION: RGD peptide sequence
<220> FEATURE:
<221> NAME/KEY: MOD_RES
<222> LOCATION: (5)..(5)
<223> OTHER INFORMATION: D-amino-acid variant of phenylalanine

<400> SEQUENCE: 29

Lys Arg Gly Asp Phe
1               5

<210> SEQ ID NO 30
<211> LENGTH: 10
<212> TYPE: PRT
<213> ORGANISM: Artificial Sequence
<220> FEATURE:
<223> OTHER INFORMATION: RGD peptide sequence
<220> FEATURE:
<221> NAME/KEY: MISC_FEATURE
<222> LOCATION: (2)..(2)
<223> OTHER INFORMATION: X = Pen = Penicillin

<400> SEQUENCE: 30

Gly Xaa Gly Arg Gly Asp Ser Pro Cys Ala
1               5                   10

<210> SEQ ID NO 31
<211> LENGTH: 5
<212> TYPE: PRT
<213> ORGANISM: Artificial Sequence
<220> FEATURE:
<223> OTHER INFORMATION: RGD peptide sequence
<220> FEATURE:
<221> NAME/KEY: MOD_RES
<222> LOCATION: (1)..(1)
<223> OTHER INFORMATION: D-amino-acid variant of valine

<400> SEQUENCE: 31

Val Arg Gly Asp Glu
1               5
```